United States Patent [19]

Kamboj et al.

[11] Patent Number: 5,614,406
[45] Date of Patent: Mar. 25, 1997

[54] KAINATE-BINDING HUMAN CNS RECEPTORS OF THE EAA2 FAMILY

[75] Inventors: Rajender Kamboj, Mississauga; Stephen L. Nutt, Etobicoke; Lee Shekter, Toronto; Michael A. Wosnick, Thornhill, all of Canada

[73] Assignee: Allelix Biopharmaceuticals Inc., Missassauga, Canada

[21] Appl. No.: 203,676

[22] Filed: Feb. 28, 1994

Related U.S. Application Data

[63] Continuation of Ser. No. 750,081, Aug. 27, 1991, abandoned.

[51] Int. Cl.[6] .............................. C12N 1/21; C12N 5/10; C12N 15/12; C12N 15/79
[52] U.S. Cl. .................. 435/325; 435/252.3; 435/320.1; 435/348; 435/354; 435/356; 435/357; 435/361; 435/364; 435/365; 435/367; 435/369; 536/23.5; 536/24.31
[58] Field of Search .............................. 435/6, 69.1, 91.2, 435/240.2, 172.3, 320.1, 240.4, 252.3; 530/350; 536/23.5, 24.31

[56] References Cited

FOREIGN PATENT DOCUMENTS

WO91/06648  5/1991  WIPO.

OTHER PUBLICATIONS

Hollmann et al, Nature (1989) 342:643.
Keinanen et al, Science (1990) 249:556.
Boulter et al, Science (1990) 249:1033.
Bettler et al, Neuron (1990) 5:583.
Sommer et al, Science (1990) 249:1580.
Monyer et al, Neuron (1991) 6:799.
Nakanishi et al, Neuron (1990) 5:569.
Hollmann et al, Science (1991) 252:851.
Verdoorn et al, Science (1991) 252:1715.
Egebjerg et al, Nature (1991) 351:745.
Wada et al, Nature (1991) 342:684.
Gregor et al, Nature (1989) 342:689.
Werner et al, Nature (1991) 351:742.
Barnett et al, Nucleic Acids Res. (1990) 18(10):3094.
William Sun, et al., "Molecular cloning, chromosomal mapping, and functional expression of human brain glutamate receptors"; Proc. Natl. Acad. Sci. USA, vol. 89, pp. 1443–1447, Feb. 1992.
Carmie Puckett, et al., "Molecular cloning and chromosomal localization of one of the human glutamate receptor genes"; Proc. Natl. Acad. Sci. USA, vol. 88, pp. 7557–7561, Sep. 1991.
Lee, C.C. et al. *Science* 239:1288–1291 (1988).
Suggs, S.V. et al. *PNAS* 78(11):6613–6617 (1981).

*Primary Examiner*—Dian C. Jacobson
*Attorney, Agent, or Firm*—Foley & Lardner

[57] ABSTRACT

Neurotransmission by excitatory amino acids (EAAs) such as glutamate is mediated via membrane-bound surface receptors. DNA coding for one family of these receptors, of the kainate binding type of EAA receptors, has now been isolated and the receptor protein characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

21 Claims, 15 Drawing Sheets

FIG. 1(a)

```
    EcoRI
      |
    GAATTCCGGCCCTGTGGACTGCCCTCTCCCCCCGCCCAGCCCCACCACCACCCAGCGCCA
  1 ---------+---------+---------+---------+---------+---------+  60
    CTTAAGGCCGGGACACCTGACGGGAGAGGGGGGCGGGTCGGGGTGGTGGTGGGTCGCGGT

BamHI
                                                                |
    GAGCCACCTCCCGCTGTCGGTCTGCGGGCCTCGAGGGAGCCCAGCCCTCCGTCCCACCAG
 61 ---------+---------+---------+---------+---------+---------+ 120
    CTCGGTGGAGGGCGACAGCCAGACGCCCGGAGCTCCCTCG GTCGGGAGG CAGGGTGGTC

SacII
                     |
    GATCCGTGGCGAGTGGGGGCCGCGGCAGCTGCGTCCCCATGAGGAGGGGAGGAAGATGCC
121 ---------+---------+---------+---------+---------+---------+ 180
    CTAGGCACCGCTCACCCCCGGCGCCGTCGACGCAGGGGTACTCCTCCCCTCCTTCTACGG

M  P
                                                          18
    GGCTGAGCTGCTGCTGCTGCTGATTGTTGCCTTCGCCAGCCCCAGCTGCCAGGTGCTCTC
181 ---------+---------+---------+---------+---------+---------+ 240
    CCGACTCGACGACGACGACGACTAACAACGGAAGCGGTCGGGGTCGACGGTCCACGAGAG

A  E  L  L  L  L  I  V  A  F  A  S  P  S  C  Q  V  L  S  4
         -15          -10            -5            |  |
                                                   |  |_Mature N-terminal
                                                   SacII
                                                     |
    ATCACTGCGCATGGCTGCAATCCTGGATGATCAGACAGTGTGTGGCCGCGGTGAGCGTCT
241 ---------+---------+---------+---------+---------+---------+ 300
    TAGTGACGCGTACCGACGTTAGGACCTACTAGTCTGTCACACACCGGCGCCACTCGCAGA

5  S  L  R  M  A  A  I  L  D  D  Q  T  V  C  G  R  G  E  R  L 24

GGCCTTGGCCTTGGCCCGGGAGCAGATCAACGGGATCATCGAGGTCCCAGCCAAGGCCCG
301 ---------+---------+---------+---------+---------+---------+ 360
    CCGGAACCGGAACCGGGCCCTCGTCTAGTTGCCCTAGTAGCTCCAGGGTCGGTTCCGGGC

25  A  L  A  L  A  R  E  Q  I  N  G  I  I  E  V  P  A  K  A  R 44

PstI
                   |
    AGTGGAAGTAGACATCTTTGAGCTGCAGCGGGACAGCCAGTACGAGACCACGGACACCAT
361 ---------+---------+---------+---------+---------+---------+ 420
    TCACCTTCATCTGTAGAAACTCGACGTCGCCCTGTCGGTCATGCTCTGGTGCCTGTGGTA

45  V  E  V  D  I  F  E  L  Q  R  D  S  Q  Y  E  T  T  D  T  M 64

GTGTCAGATCTTACCCAAAGGGGTTGTGTCTGTCCTTGGGCCCTCCTCTAGCCCAGCATC
421 ---------+---------+---------+---------+---------+---------+ 480
    CACAGTCTAGAATGGGTTTCCCCAACACAGACAGGAACCCGGGAGGAGATCGGGTCGTAG

```
          TGCCTCCACCGTGAGCCATATCTGTGGAGAGAAGGAGATCCCCCACATCAAGGTGGGTCC
    481   ---------+---------+---------+---------+---------+---------+  540
          ACGGAGGTGGCACTCGGTATAGACACCTCTCTTCCTCTAGGGGGTGTAGTTCCACCCAGG

85   A   S   T   V   S   H   I   C   G   E   K   E   I   P   H   I   K   V   G   P   104

CGAGGAGACACCCCGCCTTCAGTACCTTCGCTTCGCGTCTGTCAGCCTGTACCCCAGTAA
    541   ---------+---------+---------+---------+---------+---------+  600
          GCTCCTCTGTGGGGCGGAAGTCATGGAAGCGAAGCGCAGACAGTCGGACATGGGGTCATT

105   E   E   T   P   R   L   Q   Y   L   R   F   A   S   V   S   L   Y   P   S   N   124

CGAGGACGTCAGCTTGGCGGTCTCCCGAATCCTCAAGTCCTTCAACTACCCCTCGGCCAG
    601   ---------+---------+---------+---------+---------+---------+  660
          GCTCCTGCAGTCGAACCGCCAGAGGGCTTAGGAGTTCAGGAAGTTGATGGGGAGCCGGTC

125   E   D   V   S   L   A   V   S   R   I   L   K   S   F   N   Y   P   S   A   S   144

CCTCATCTGCGCCAAGGCTGAGTGCCTGCTGCGATTGGAGGAACTGGTGCGTGGCTTCCT
    661   ---------+---------+---------+---------+---------+---------+  720
          GGAGTAGACGCGGTTCCGACTCACGGACGACGCTAACCTCCTTGACCACGCACCGAAGGA

145   L   I   C   A   K   A   E   C   L   L   R   L   E   E   L   V   R   G   F   L   164

CATCTCCAAGGAGACGCTGTCAGTGAGGATGTTGGACGACAGCCGGGACCCCACACCACT
    721   ---------+---------+---------+---------+---------+---------+  780
          GTAGAGGTTCCTCTGCGACAGTCACTCCTACAACCTGCTGTCGGCCCTGGGGTGTGGTGA

165   I   S   K   E   T   L   S   V   R   M   L   D   D   S   R   D   P   T   P   L   184

GCTCAAGGAGATCCGTGATGACAAGGTGTCCACCATCATCATCGACGCCAACGCCTCCAT
    781   ---------+---------+---------+---------+---------+---------+  840
          CGAGTTCCTCTAGGCACTACTGTTCCACAGGTGGTAGTAGTAGCTGCGGTTGCGGAGGTA

185   L   K   E   I   R   D   D   K   V   S   T   I   I   I   D   A   N   A   S   I   204

CTCCCACCTCATCCTCCGTAAGGCCTCGGAACTGGGAATGACCTCAGCGTTTTACAAGTA
    841   ---------+---------+---------+---------+---------+---------+  900
          GAGGGTGGAGTAGGAGGCATTCCGGAGCCTTGACCCTTACTGGAGTCGCAAAATGTTCAT

205   S   H   L   I   L   R   K   A   S   E   L   G   M   T   S   A   F   Y   K   Y   224
                          NcoI
          CATCCTCACCACCATGGACTTCCCCATCCTGCATCTGGACGGTATTGTGGAGGACTCCTC
    901   ---------+---------+---------+---------+---------+---------+  960
          GTAGGAGTGGTGGTACCTGAAGGGGTAGGACGTAGACCTGCCATAACACCTCCTGAGGAG

225   I   L   T   T   M   D   F   P   I   L   H   L   D   G   I   V   E   D   S   S   244

CAACATCCTGGGCTTCTCCATGTTCAACACGTCCCACCCCTTCTACCCTGAGTTTGTCCG
    961   ---------+---------+---------+---------+---------+---------+ 1020
          GTTGTAGGACCCGAAGAGGTACAAGTTGTGCAGGGTGGGGAAGATGGGACTCAAACAGGC

```
     CAGCCTCAACATGTCCTGGAGGGAGAACTGTGAAGCCAGCACCTACCTGGGCCCTGCGCT
1021 ---------+---------+---------+---------+---------+---------+ 1080
     GTCGGAGTTGTACAGGACCTCCCTCTTGACACTTCGGTCGTGGATGGACCCGGGACGCGA

265   S  L  N  M  S  W  R  E  N  C  E  A  S  T  Y  L  G  P  A  L  284

GTCAGCCGCCCTGATGTTTGACGCCGTGCACGTGGTGGTGAGCGCTGTCCGAGAGCTGAA
1081 ---------+---------+---------+---------+---------+---------+ 1140
     CAGTCGGCGGGACTACAAACTGCGGCACGTGCACCACCACTCGCGACAGGCTCTCGACTT

285   S  A  A  L  M  F  D  A  V  H  V  V  V  S  A  V  R  E  L  N  304

CCGCAGCCAGGAGATCGGTGTGAAGCCTCTGGCCTGTACATCGGCCAACATTTGGCCCCA
1141 ---------+---------+---------+---------+---------+---------+ 1200
     GGCGTCGGTCCTCTAGCCACACTTCGGAGACCGGACATGTAGCCGGTTGTAAACCGGGGT

306   R  S  Q  E  I  G  V  K  P  L  A  C  T  S  A  N  I  W  P  H  324

CGGGACCAGCCTCATGAACTACCTGCGCATGGTAGAGTATGATGGGCTGACCGGGCGGGT
1201 ---------+---------+---------+---------+---------+---------+ 1260
     GCCCTGGTCGGAGTACTTGATGGACGCGTACCATCTCATACTACCCGACTGGCCCGCCCA

325   G  T  S  L  M  N  Y  L  R  M  V  E  Y  D  G  L  T  G  R  V  344

CGAGTTCAACAGCAAAGGGCAGAGAACCAACTACACCCTGCGCATCCTAGAAAAGTCCCG
1261 ---------+---------+---------+---------+---------+---------+ 1320
     GCTCAAGTTGTCGTTTCCCGTCTCTTGGTTGATGTGGGACGCGTAGGATCTTTTCAGGGC

345   E  F  N  S  K  G  Q  R  T  N  Y  T  L  R  I  L  E  K  S  R  364

GCAGGGCCACCGTGAGATTGGGGTGTGGTACTCTAACCGCACCCTGGCCATGAATGCCAC
1321 ---------+---------+---------+---------+---------+---------+ 1380
     CGTCCCGGTGGCACTCTAACCCCACACCATGAGATTGGCGTGGGACCGGTACTTACGGTG

365   Q  G  H  R  E  I  G  V  W  Y  S  N  R  T  L  A  M  N  A  T  384

CACCCTGGACATCAACCTGTCGCAGACACTGGCCAACAAGACCCTGGTGGTCACAACCAT
1381 ---------+---------+---------+---------+---------+---------+ 1440
     GTGGGACCTGTAGTTGGACAGCGTCTGTGACCGGTTGTTCTGGGACCACCAGTGTTGGTA

385   T  L  D  I  N  L  S  Q  T  L  A  N  K  T  L  V  V  T  T  I  404

CCTGGAGAACCCATACGTCATGCGCCGGCCCAACTTCCAGGGCCTGTCGGGGAACGAACG
1441 ---------+---------+---------+---------+---------+---------+ 1500
     GGACCTCTTGGGTATGCAGTACGCGGCCGGGTTGAAGGTCCCGGACAGCCCCTTGCTTGC

405   L  E  N  P  Y  V  M  R  R  P  N  F  Q  G  L  S  G  N  E  R  424

CTTCGAGGGCTTCTGCGTGGACATGCTGCGGGAGCTGGCCGAGCTGCTGCCGTTCCCGTA
1501 ---------+---------+---------+---------+---------+---------+ 1560
     GAAGCTCCCGAAGACGCACCTGTACGACGCCCTCGACCGGCTCGACGACGGCAAGGGCAT

```
     CCGCCTGCGGTTGGTGGAGGATGGGCTGTACGGGGCGCCCGAGCCCAACGGCTCCTGGAC
1561 ---------+---------+---------+---------+---------+---------+ 1620
     GGCGGACGCCAACCACCTCCTACCCGACATGCCCCGCGGGCTCGGGTTGCCGAGGACCTG

445   R  L  R  L  V  E  D  G  L  Y  G  A  P  E  P  N  G  S  W  T  464

SacI
                       |
     GGGCATGGTTGGCGAGCTCATCAACCGGAAGGCAGACCTGGCTGTGGCCGCCTTCACCAT
1621 ---------+---------+---------+---------+---------+---------+ 1680
     CCCGTACCAACCGCTCGAGTAGTTGGCCTTCCGTCTGGACCGACACCGGCGGAAGTGGTA

465   G  M  V  G  E  L  I  N  R  K  A  D  L  A  V  A  A  F  T  I  484

CACAGCTGAGCGGGAGAAGGTCATCGACTTTTCCAAGCCCTTTATGACCCTGGGGATCAG
1681 ---------+---------+---------+---------+---------+---------+ 1740
     GTGTCGACTCGCCCTCTTCCAGTAGCTGAAAAGGTTCGGGAAATACTGGGACCCCTAGTC

485   T  A  E  R  E  K  V  I  D  F  S  K  P  F  M  T  L  G  I  S  504

CATCCTCTACCGAGTGCACATGGGCCGCAAGCCTGGCTACTTCTCCTTCCTGGACCCCTT
1741 ---------+---------+---------+---------+---------+---------+ 1800
     GTAGGAGATGGCTCACGTGTACCCGGCGTTCGGACCGATGAAGAGGAAGGACCTGGGGAA

505   I  L  Y  R  V  H  M  G  R  K  P  G  Y  F  S  F  L  D  P  F  524

CTCCCCTGCTGTGTGGCTCTTCATGCTTCTTGCCTACCTGGCTGTCAGCTGCGTCCTGTT
1801 ---------+---------+---------+---------+---------+---------+ 1860
     GAGGGGACGACACACCGAGAAGTACGAAGAACGGATGGACCGACAGTCGACGCAGGACAA

525   S  P  A  V  W  L  F  M  L  L  A  Y  L  A  V  S  C  V  L  P  544

TCTGGCTGCCAGGCTGAGCCCCTATGAGTGGTATAACCCACACCCATGCCTGCGGGCACG
1861 ---------+---------+---------+---------+---------+---------+ 1920
     AGACCGACGGTCCGACTCGGGGATACTCACCATATTGGGTGTGGGTACGGACGCCCGTGC

545   L  A  A  R  L  S  P  Y  E  W  Y  N  P  H  P  C  L  R  A  R  564

CCCCCACATCCTGGAGAACCAGTACACGCTGGGCAACAGCCTGTGGTTTCCCGTGGGGGG
1921 ---------+---------+---------+---------+---------+---------+ 1980
     GGGGGTGTAGGACCTCTTGGTCATGTGCGACCCGTTGTCGGACACCAAAGGGCACCCCCC

565   P  H  I  L  E  N  Q  Y  T  L  G  N  S  L  W  F  P  V  G  G  584

CTTCATGCAGCAGGGCTCGGAGATCATGCCCCGGGCGCTGTCCACGCGCTGTGTCAGCGG
1981 ---------+---------+---------+---------+---------+---------+ 2040
     GAAGTACGTCGTCCCGAGCCTCTAGTACGGGGCCCGCGACAGGTGCGCGACACAGTCGCC

585   F  M  Q  Q  G  S  E  I  M  P  R  A  L  S  T  R  C  V  S  G  604

AGTCTGGTGGGCCTTCACCTTGATCATCATCTCCTCCTACACGGCCACCCTGGCCGCCTT
2041 ---------+---------+---------+---------+---------+---------+ 2100
     TCAGACCACCCGGAAGTGGAACTAGTAGTAGAGGAGGATGTGCCGGTGGGACCGGCGGAA

```
      CCTCACCGTGCAGCGCATGGAGGTGCCTGTGGAGTCGGCCGATGACCTGGCAGATCAGAC
2101  ------------+----------+----------+----------+----------+----------+  2160
      GGAGTGGCACGTCGCGTACCTCCACGGACACCTCAGCCGGCFACTGGACCGTCTAGTCTG

625    L   T   V   Q   R   M   E   V   P   V   E   S   A   D   D   L   A   D   Q   T    644
                                                                    EcoRI
                                                                      |
      CAACATCGAGTATGGCACCATCCACGCCGGCTCCACCATGACCTTCTTCCAGAATTCACG
2161  ------------+----------+----------+----------+----------+----------+  2220
      GTTGTAGCTCATACCGTGGTAGGTGCGGCCGAGGTGGTACTGGAAGAAGGTCTTAAGTGC

645    N   I   E   Y   G   T   I   H   A   G   S   T   M   T   F   F   Q   N   S   R    664
              KpnI
                |
      GTACCAAACGTACCAGCGCATGTGGAACTACATGCAGTCGAAGCAGCCCAGCGTGTTCGT
2221  ------------+----------+----------+----------+----------+----------+  2280
      CATGGTTTGCATGGTCGCGTACACCTTGATGTACGTCAGCTTCGTCGGGTCGCACAAGCA

665    Y   Q   T   Y   Q   R   M   W   N   Y   M   Q   S   K   Q   P   S   V   F   V    684

CAAGAGCACAGAAGAGGGCATTGCCGCCGTCCTCAACTCCCGCTACGCCTTCCTGCTCGA
2281  ------------+----------+----------+----------+----------+----------+  2340
      GTTCTCGTGTCTTCTCCCGTAACGGCGGCAGGAGTTGAGGGCGATGCGGAAGGACGAGCT

685    K   S   T   E   E   G   I   A   A   V   L   N   S   R   Y   A   F   L   L   E    704

GTCCACCATGAACGAATACCACCGGCGCCTCAACTGCAACCTCACCCAGATCGGGGGACT
2341  ------------+----------+----------+----------+----------+----------+  2400
      CAGGTGGTACTTGCTTATGGTGGCCGCGGAGTTGACGTTGGAGTGGGTCTAGCCCCCTGA

705    S   T   M   N   E   Y   H   R   R   L   N   C   N   L   T   Q   I   G   G   L    724
                                      SphI
                                        |
      CCTCGACACCAAGGGCTACGGCATTGGCATGCCGCTGGGCTCCCCGTTCCGGGATGAGAT
2401  ------------+----------+----------+----------+----------+----------+  2460
      GGAGCTGTGGTTCCCGATGCCGTAACCGTACGGCGACCCGAGGGGCAAGGCCCTACTCTA

725    L   D   T   K   G   Y   G   I   G   M   P   L   G   S   P   F   R   D   E   I    744
                              PstI
                                |
      CACACTGGCCATCCTGCAGCTTCAGGAGAACAACCGGCTGGAGATCCTGAAGCGCAAGTG
2461  ------------+----------+----------+----------+----------+----------+  2520
      GTGTGACCGGTAGGACGTCGAAGTCCTCTTGTTGGCCGACCTCTAGGACTTCGCGTTCAC

745    T   L   A   I   L   Q   L   Q   E   N   N   R   L   E   I   L   K   R   K   W    764

GTGGGAGGGGGGCCGGTGCCCCAAGGAGGAGGACCATCGAGCTAAAGGTTTGGGCATGGA
2521  ------------+----------+----------+----------+----------+----------+  2580
      CACCCTCCCCCCGGCCACGGGGTTCCTCCTCCTGGTAGCTCGATTTCCAAACCCGTACCT

```
     GAACATTGGTGGCATTTTTATCGTGCTCATCTGTGGCCTCATCATTGCTGTCTTCGTGGC
2581 ---------+---------+---------+---------+---------+---------+ 2640
     CTTGTAACCACCGTAAAAATAGCACGAGTAGACACCGGAGTAGTAACGACAGAAGCACCG

785   N  I  G  G  I  F  I  V  L  I  C  G  L  I  I  A  V  F  V  A   804

EcoRI
                |
     GGTCATGGAATTCATATGGTCCACACGGAGGTCAGCTGAGTCCGAGGAGTGTCGGTGTG
2641 ---------+---------+---------+---------+---------+---------+ 2700
     CCAGTACCTTAAGTATACCAGGTGTGCCTCCAGTCGACTCAGGCTCCTCACAGCCACAC

805   V  M  E  F  I  W  S  T  R  R  S  A  E  S  E  E  V  S  V  C   824

PstI
                        |
     CCAGGAGATGCTGCAGGAGCTGCGCCACGCCGTTTCTTGCCGCAAGACGTCGCGTTCCCG
2701 ---------+---------+---------+---------+---------+---------+ 2760
     GGTCCTCTACGACGTCCTCGACGCGGTGCGGCAAAGAACGGCGTTCTGCAGCGCAAGGGC

825   Q  E  M  L  Q  E  L  R  H  A  V  S  C  R  K  T  S  R  S  R   844

CCGGCGCCGACGCCCGGGCGGCCCGAGCCGGGCCCTGCTGTCACTGCGCGCGGTCCGCGA
2761 ---------+---------+---------+---------+---------+---------+ 2820
     GGCCGCGGCTGCGGGCCCGCCGGGCTCGGCCCGGGACGACAGTGACGCGCGCCAGGCGCT

845   R  R  R  R  P  G  G  P  S  R  A  L  L  S  L  R  A  V  R  E   864

GATGCGCCTCAGCAACGGCAAGCTCTACTCGGCCGGCGCGGGCGGGGATGCGGGCAGCGC
2821 ---------+---------+---------+---------+---------+---------+ 2880
     CTACGCGGAGTCGTTGCCGTTCGAGATGAGCCGGCCGCGCCCGCCCCTACGCCCGTCGCG

865   M  R  L  S  N  G  K  L  Y  S  A  G  A  G  G  D  A  G  S  A   884

GCACGGGGGCCCGCAGCGCCTCCTGGACGACCCGGGGCCCCCCAGCGGAGCCCGACCCGC
2881 ---------+---------+---------+---------+---------+---------+ 2940
     CGTGCCCCCGGGCGTCGCGGAGGACCTGCTGGGCCCCGGGGGGTCGCCTCGGGCTGGGCG

885   H  G  G  P  Q  R  L  L  D  D  P  G  P  P  S  G  A  R  P  A   904

CGCCCCCACCCCCTGCACCCACGTGCGCGTCTGCCAGGAGTGCCGGCGCATCCAGGCGCT
2941 ---------+---------+---------+---------+---------+---------+ 3000
     GCGGGGGTGGGGGACGTGGGTGCACGCGCAGACGGTCCTCACGGCCGCGTAGGTCCGCGA

905   A  P  T  P  C  T  H  V  R  V  C  Q  E  C  R  R  I  Q  A  L   924

GCGGGCCTCGGGGGCCGGCGCGCCTCCGCGTGGCCTGGGCGTCCCCGCCGAAGCCACCAG
3001 ---------+---------+---------+---------+---------+---------+ 3060
     CGCCCGGAGCCCCCGGCCGCGCGGAGGCGCACCGGACCCGCAGGGGCGGCTTCGGTGGTC

925   R  A  S  G  A  G  A  P  P  R  G  L  G  V  P  A  E  A  T  S   944

SacII
                          |
     CCCGCCCCGGCCGCGGCCTGGCCCCGCCGGCCCCCGGGAGCTGGCGGAGCACGAGTGACC
3061 ---------+---------+---------+---------+---------+---------+ 3120
     GGGCGGGGCCGGCGCCGGACCGGGGCGGCCGGGGGCCCTCGACCGCCTCGTGCTCACTGG

```
      ACGGGCGGGGCTGTGCGGGCGCCCGGACTGACCGAAGGGACGGGGCCCGCCCCAGGCCCC
3121  ---------+---------+---------+---------+---------+---------+  3180
      TGCCCGCCCCGACACGCCCGCGGGCCTGACTGGCTTCCCTGCCCCGGGCGGGGTCCGGGG

AGCAGTCTCCGCTCCCGCAGCGGGCGCGGGACAGGACTGGTGCGCCGGCGCCCCGGACGC
3181  ---------+---------+---------+---------+---------+---------+  3240
      TCGTCAGAGGCGAGGGCGTCGCCCGCGCCCTGTCCTGACCACGCGGCCGCGGGGCCTGCG

CGCGATTTTGCCTTTGGTTCCCCGCGAAGTCCGAGGCCTGGCTCTGGACCCCGCCTGCGC
3241  ---------+---------+---------+---------+---------+---------+  3300
      GCGCTAAAACGGAAACCAAGGGGCGCTTCAGGCTCCGGACCGAGACCTGGGCGGACGCG

SacII
                              |
      CCCCCAGTGGACTCGCGAGAGGGTGCCGCGGGCGAGAAGGGCGCAGGAACCGAGGACTCC
3301  ---------+---------+---------+---------+---------+---------+  3360
      GGGGGTCACCTGAGCGCTCTCCCACGGCGCCCGCTCTTCCCGCGTCCTTGGCTCCTGAGG

AGGGGCTGGGGACTTCGGGGGCGGCTCTGGGAAGCGGAAAGCAGTCAGCGGAGAGGACCC
3361  ---------+---------+---------+---------+---------+---------+  3420
      TCCCCGACCCCTGAAGCCCCCGCCGAGACCCTTCGCCTTTCGTCAGTCGCCTCTCCTGGG

CATTCTGGGACTGCTCAGGCTCCCCAAGACTTGACGCAGCCCCCCACGCTTCTGAGGTGG
3421  ---------+---------+---------+---------+---------+---------+  3480
      GTAAGACCCTGACGAGTCCGAGGGGTTCTGAACTGCGTCGGGGGGTGCGAAGACTCCACC

GGAGGGCCTCTGGACAGATGGGTGTCCCCTGGTGCCCCTCCACTCTTCTCTTCCTCTCTT
3481  ---------+---------+---------+---------+---------+---------+  3540
      CCTCCCGGAGACCTGTCTACCCACAGGGGACCACGGGGAGGTGAGAAGAGAAGGAGAGAA

TTTTGGGGGGAGAAACCTCGGAATTTCTATGAGACCTCCCCCAGGGAGGGGGTCAGTTGG
3541  ---------+---------+---------+---------+---------+---------+  3600
      AAAACCCCCCTCTTTGGAGCCTTAAAGATACTCTGGAGGGGGTCCCTCCCCCAGTCAACC

GCCCCCATCCCTCCCCTTGCCACATCGCAGCCCCTGTTGGAATAAAAAAAAGAACAAAAG
3601  ---------+---------+---------+---------+---------+---------+  3660
      CGGGGGTAGGGAGGGGAACGGTGTAGCGTCGGGGACAACCTTATTTTTTTTCTTGTTTTC

EcoRI
                    |
      GGGAAAAAAAAAAAAAAAAAAAAAAAAAAAAGGAATTC
3661  ---------+---------+---------+-----      3695
      CCCTTTTTTTTTTTTTTTTTTTTTTTTTTTTCCTTAAG
```

FIG. 4(a)

PARTIAL NUCLEOTIDE AND AMINO ACID COMPARISON
BETWEEN HUM EAA2a AND HUM EAA2b

```
Hum EAA2b  466  MetValGlyGluLeuIleAsnArgGlnLysAlaAspLeuAlaAlaValAla  481
          1625  ATGGTTGGGCGAGCTCATCAACCGGCAGAAGGCAGACCTGGCTGTGGCC   1672
                |||||||||||||||||||||||||||||     |||||||||||||||
          1625  ATGGTTGGGCGAGCTCATCAACCGG_____AAGGCAGACCTGGCTGTGGCC 1669
Hum EAA2a  466  MetValGlyGluLeuIleAsnArg___LysAlaAspLeuAlaValAla   480
```

FIG. 4(b)

PARTIAL NUCLEOTIDE (UPPER PANEL) AND AMINO ACID (LOWER PANEL) COMPARISON OF HUM EAA2a AND HUM EAA2c

```
Hum EAA2a    226 CTGCCAGGTGCTCTCATCACTGCGCATGGCTGCAATCCTGGATGATCAGA   275
                            |        | | |    |
Hum EAA2c      8 ---------------------GGATGAGGCACAAGAATCACTTGGACCGG    36

HumEAA2a     276 CAGTGTGTGGCCGCGGTGAGCGTCTGGCCTTGGCCTTGGCCCGGGAGCAG   325
                 ||   |    |   ||  |||||||||||||||||||||||||||||||||
HumEAA2c      37 GAGGCAGGAGTTGCAGTGAGCGTCTGGCCTTGGCCTTGGCCCGGGAGCAG    86
```

```
                 I-Signal Peptide- II- Mature N-Terminal
Hum EAA2a        MPAELLLLLIVAFASPSCQVLSSLRMAAILDDQTVCGRGERLALALA        29
                                           | _  ---- = =||||||||
Hum EAA2c        ----------------------DEAQESLGPGGRSCSERLALALA         23

Hum EAA2a     30 REQINGIIEVPAKARVEVDIFELQRDSQYETTDTMCQILPK      70
                 ||||||||||||||||||||||||||||||||||||||||
Hum EAA2c     24 REQINGIIEVPAKARVEVDIFELQRDSQYETTDTMCQILPK      64
```

Hum EAA 2 Gene Family

Scatchard Plot of (3H) Kainate binding to Clone 2a

Saturation Analysis of (3H) Kainate Binding to Clone 2a

DISPLACEMENT OF (3H) KAINATE BINDING TO HumEAA2a RECEPTORS

| COMPOUND | IC50 (M) | $K_i$ (nM) | HILL COEFF | CORR. COEFF. |
|---|---|---|---|---|
| KAINATE | 4.26E-09 | 1.56 | 0.795 | 0.904 |
| DOMOATE | 3.44E-08 | 12.6 | 0.431 | 0.962 |
| QUISQUALATE | 5.95E-08 | 21.8 | 0.692 | 0.801 |
| L-GLUTAMATE | 3.10E-07 | 114 | 1.170 | 0.875 |
| DNQX | 4.22E-06 | 1550 | 1.234 | 1.000 |
| DIHYDROKAINATE | 5.36E-06 | 1970 | 0.785 | 0.946 |
| CNQX | 5.39E-06 | 1980 | 0.674 | 0.985 |
| AMPA | 8.27E-06 | 3040 | 1.110 | 0.967 |
| 1S.3R-ACPD | — | >100000 | — | — |
| NMDA | — | >100000 | — | — |

KAINATE-BINDING HUMAN CNS RECEPTORS OF THE EAA2 FAMILY

This application is a continuation of application Ser. No. 07/750,081, filed Aug. 27, 1991, now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impulses is controlled by the interaction between a neurotransmitter substance released by the "sending" neuron and a surface receptor on the "receiving" neuron. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

This family of glutamate-binding EAA receptors is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered, Hollmann et al., Nature 342:643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249:556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249:1033, 1990, revealed that, in addition to GluR1, the rat contained 3 other related genes, which they called GluR2, GluR3, and GluR4, and Bettler et al., Neuron 5:583, 1990 described Glu5. Keinanen et al., supra, described genes called GluR-A, GluR-B, GluR-C and GluR-D which correspond precisely to GluR1, GluR2, GluR3 and GluR4 respectively, Sommer et al., Science 249:1580, 1990 also showed, for GluR-A, GluR-B, GluR-C and GluR-D two alternatively spliced forms for each gene. These authors, as well as Monyer et al., Neuron 6:799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5:569, 1990; Hollman et al., Science 252:851, 1991; Verdoorn et al., Science 252:1715, 1991; and see WO 91/06648).

Some recent work has also been published regarding non-human genes which appear to encode the kainate-type of receptor. Egebjerg et al., Nature 351:745, 1991, have described the isolation of a gene from rat called GluR6, which although related in sequence to the AMPA receptor genes, forms a receptor which is not activated by AMPA but rather by glutamate, quisqualate, and preferentially, kainate. Other kainate-binding proteins have been described from frog (Wada et al., Nature 342:684, 1989), chicken (Gregor et al., Nature 342:689, 1989) and from rat (Werner et al., Nature 351:742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA2a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA2a receptor have also been identified, and constitute additional members of this receptor family, herein referred to as the human EAA2 receptor family.

The present invention thus provides, in one of its aspects, an isolated polynucleotide, consisting either of DNA or of RNA, which codes for a human EAA2 receptor or for a kainate-binding fragment thereof.

In another aspect of the present invention, there is provided a cell that has been genetically engineered to produce a kainate-binding, human EAA receptor belonging to the herein-defined EAA2 family. In related aspects of the present invention, there are provided recombinant DNA constructs and relevant methods useful to create such cells.

In another aspect of the present invention, there is provided a method for evaluating the the affinity of a selected compound for binding to a receptor having the characteristics of a human EAA2 receptor, which comprises the steps of incubating the compound with a genetically engineered cell of the present invention, or with a membrane preparation derived therefrom, in a manner suitable to determine the receptor binding affinity of the test compound.

Other aspects of the present invention, which encompass various applications of the discoveries herein described, will become apparent from the following detailed description, and from the accompanying drawings.

BRIEF REFERENCE TO THE DRAWINGS

FIGS. 1(a)–1(g) provide the nucleotide sequence (SEQ. ID NO: 1) of DNA coding for an excitatory amino acid receptor of the present invention, and the deduced amino acid sequence (SEQ. ID. NO: 2) thereof;

FIG. 2 illustrates schematically a PCR-based strategy for amplifying the DNA sequence illustrated in FIGS. 1(a)–1(g) (Primers 1–8 are shown in SEQ. ID NOs. 3–10, respectively);

FIGS. 3(a) and 3(b) illustrate with linear plasmid maps the strategy used to construct expression vectors harbouring the DNA sequence illustrated in FIGS. 1(a)–1(g) (The sequences shown in FIG. 3(2) are also disclosed in SEQ ID NOs. 11 and 12);

FIGS. 4(a), (SEQ ID NOs 13–18) 4(b) (SEQ ID NOS: 19–22) and 4(c) show, with reference to FIG. 1, the DNA and amino acid sequences of naturally occurring variants of the EAA receptor illustrated in FIG. 1(a)–1(g);

FIGS. 5(a) and 5(b) and FIG. 6 illustrate graphically the ligand-binding properties of the EAA receptor expressed from the coding region provided in FIGS. 1(a)–1(g).

DETAILED DESCRIPTION OF THE INVENTION AND ITS PREFERRED EMBODIMENTS

Figure 2:
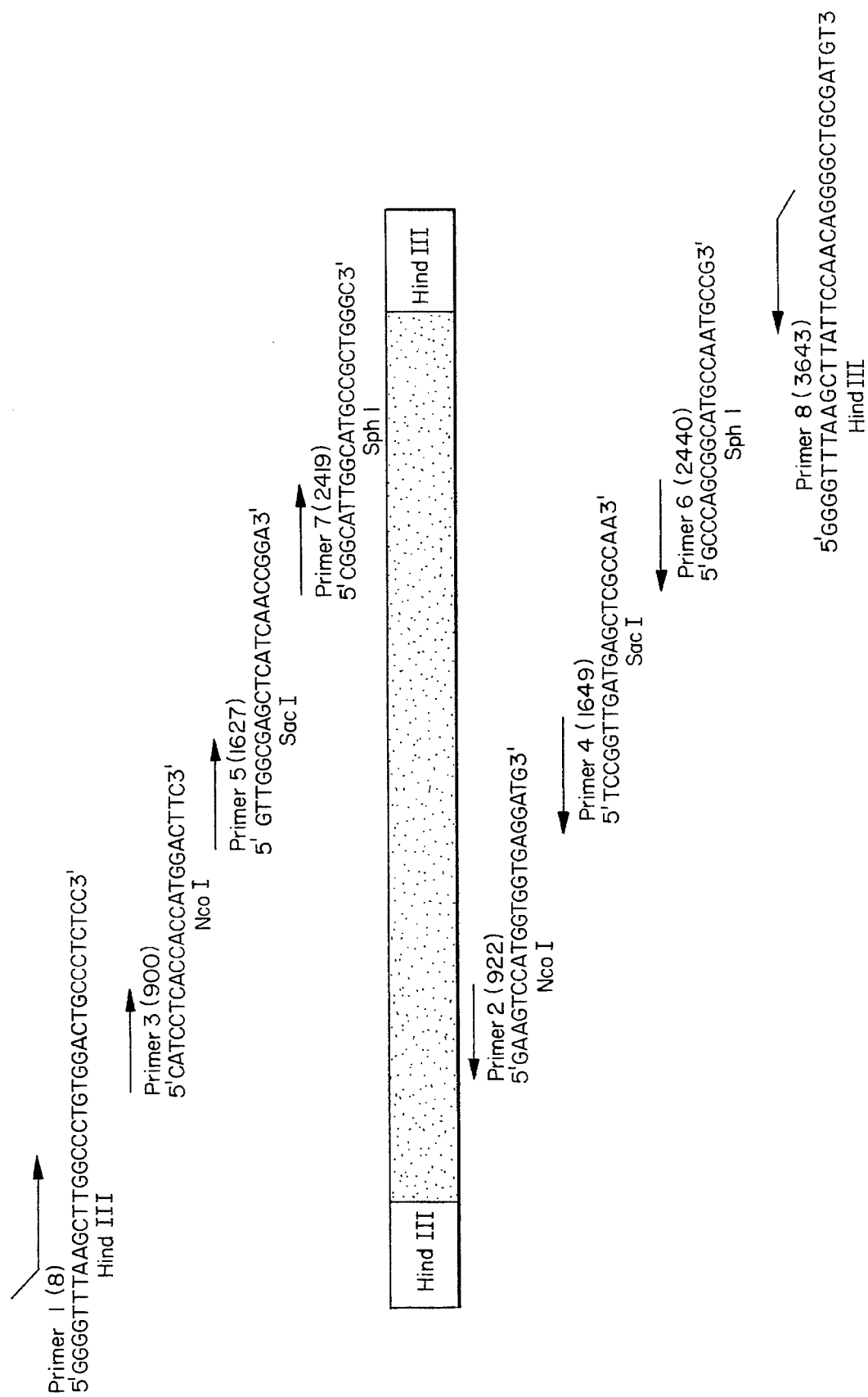

The invention relates to excitatory amino acid (EAA) receptors of human origin, and is directed more particularly to a novel family of kainate-type human EAA receptors, herein designated the human EAA2 receptor family. As used herein, the term "human EAA2 receptor" is intended to embrace the human EAA2a receptor, and kainate-binding variants of the EAA2a receptor that are structurally related thereto, i.e. have at least 95% homology therewith, including naturally occurring and synthetically derived variants of the EAA2a receptor. Naturally occurring variants of the human EAA2a receptor include particularly the receptors herein designated human EAA2b receptor, and human EAA2c receptor. As used herein, the term "kainate-binding" refers EAA2b receptor, and human EAA2c receptor. As used herein, the term "kainate-binding" refers to receptor variants and receptor fragments that display greater binding affinity for kainate than for either glutamate, AMPA or NMDA, as determined in assays of conventional design, such as the assays herein described.

The particular human EAA receptor designated EAA2a is a protein characterized structurally as a single polypeptide chain that is produced initially in precursor form bearing an 18 residue N-terminal signal peptide, and is transported to the cell surface in mature form, lacking the signal peptide and consisting of 962 amino acids arranged in the sequence illustrated, by single letter code, in FIGS. 1(a)–1(g). Unless otherwise stated, amino acid residues of the EAA2a receptor are numbered with reference to the mature protein sequence. With respect to structural domains of the receptor, hydropathy analysis reveals four putative transmembrane domains, one spanning residues 528–547 inclusive (TM-1), another spanning residues 572–590 (TM-2), a third spanning residues 601–619 (TM-3) and the fourth spanning residues 786–806 (TM-4). Based on this assignment, it is likely that the human EAA2a receptor structure, in its natural membrane-bound form, consists of a 527 amino acid N-terminal extracellular domain, followed by a hydrophobic region containing four transmembrane domains and an extracellular, 156 amino acid C-terminal domain.

As shown in FIG. 4, structurally related variants of the EAA2a receptor, which occur naturally in human brain tissue, have also been identified. As deduced from nucleotide sequences of the genes coding for them, these variants differ structurally therefrom by the insertion of one additional amino acid between positions 473 and 474 of EAA2a, in the case of EAA2b. The other variant, designated EAA2c, differs from EAA2a by fifteen amino acids in the N-terminal region (FIG. 4).

In human hippocampal cDNA libraries, the source from which DNA coding for the EAA2a receptor was isolated, the EAA2a receptor is encoded by the nucleotide sequence provided in FIG. 1. Relative to nucleic acid sequences that code for excitatory amino acid receptors discovered in rat tissue, as described in the publications mentioned hereinabove, the human EAA2a receptor shares limited nucleic acid sequence identity, at best approximately 60%. This vast structural difference suggests that non-human counterparts of EAA2a remain to be discovered, or perhaps are non-existent.

Like other members of the human EAA2 receptor family, receptor subtype EAA2a is characterized by a pharmacological profile i.e. a ligand binding "signature", that points strongly to a kainate-type pharmacology, as distinct from other excitatory amino acid receptor types, such as NMDA and AMPA. Despite the understanding that kainate binding receptors require a multi-and perhaps heteromeric subunit structure to function in the pharmacological sense, it has been found that cells producing the unitary EAA2a receptor do, independently of association with other receptor subunits, provide a reliable indication of excitatory amino acid binding. Thus, in a key aspect of the present invention, the human EAA2a receptor is exploited for the purpose of screening candidate compounds for the ability to compete with endogenous EAA receptor ligands and known synthetic analogues thereof, for EAA receptor binding.

For use in receptor binding assays, it is desirable to construct by application of genetic engineering techniques a mammalian cell that produces the EAA2a receptor in functional form as a heterologous product. The construction of such cell lines is achieved by introducing into a selected host cell a recombinant DNA construct in which DNA coding for the human EAA2a receptor in a form transportable to the cell surface i.e., bearing its native signal peptide or a functional, heterologous equivalent thereof, is associated with expression controlling elements that are functional in the selected host to drive expression of the receptor-encoding DNA, and thus elaborate the desired EAA2 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human EAA2a receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cell may nevertheless serve as expression hosts, provided that "background" binding to the test ligand is accounted for the assay results.

According to one embodiment of the present invention, the cell line selected to serve as host for EAA2 receptor production is a mammalian cell. Several types of such cell lines are currently available for genetic engineering work, and these include the chinese hamster ovary (CHO) cell for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651; murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the EAA2 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the transportable receptor precursor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as E. coli. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heave metals, i.e., the metalothionein gene promoter, and other steroid-inducible promoters.

For incorporation into the recombinant DNA expression vector, DNA coding for the desired EAA2 receptor, i.e. the EAA2a receptor or a kainate-binding variant thereof, can be obtained by applying selected techniques of gene isolation or gene synthesis. As described in more detail in the examples herein, the EAA2a receptor, and the EAA2b and EAA2c variants thereof, are encoded within the genome of human brain tissue, and can therefore be obtained by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in, for example, a bacterial plasmid, more typically a bacteriophage. Such bacteriophage harbouring fragments of the human DNA are typically grown by plating on a lawn of susceptible E. coli bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA2 receptors, it will be appreciated that automated techniques of gene synthesis and/or amplification can be performed to generate DNA coding therefor. Because of the length of the EAA2 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA2 gene family. It will be appreciated, for example, that polynucleotides coding for the EAA2 receptors herein described can be generated by substituting synonymous codons for those represented in the naturally occurring polynucleotide sequences herein identified. In addition, polynucleotides coding for synthetic variants of the EAA2 receptors herein described can be generated which, for example, incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity, e.g., within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the E. coli gpt gene which confers resistance to mycophenolic acid, the neo gene from transposon Tn5 which confers resistance to the antibiotic G418 and to neomycin, the dhfr sequence from murine cells or E. coli which changes the phenotype of DHFR–cells into DHFR+cells, and the tk gene of herpes simplex virus, which makes TK–cells phenotypically TK+cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human EAA2 receptor of the invention is evaluated typically using a predetermined amount of cell-derived membrane (measured for example by protein determination), generally from about 25 μg to 100 μg. Generally, competitive binding assays will be useful to evaluate the affinity of a test compound relative to kainate. This competitive binding assay can be performed by incubating the membrane preparation with radiolabelled kainate, for example [3H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

As an alternative to using cells that express receptor-encoding DNA, ligand characterization may also be performed using cells, for example Xenopus oocytes, that yield functional membrane-bound receptor following introduction of messenger RNA coding for the EAA2 receptor. In this case, the EAA2 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the EAA2 receptor responsible for binding a ligand molecule resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length EAA2 receptor-encoding DNA may be modified by site-directed mutagenesis, so as to introduce a translational stop codon into the extracellular N-terminal region, immediately before the sequence encoding the first transmembrane domain (TM1), i.e., before residue 528 as shown in FIGS. 1(a)-1(g). Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 806 and 962 inclusive of FIGS. 1(a)-1(g). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (Spodoptera frugiperda) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. Aspergillus nidulans, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100–130 amino acids in length, then the powerful technique of 2-D NMR can also be applied to structure determination. This enables not only the determination of the domain structure, but also provides dynamic information about the drug-receptor interaction.

For use particularly in detecting the presence and/or location of an EAA2 receptor, for example in brain tissue, the present invention also provides, in another of its aspects, labelled antibody to a human EAA2 receptor. To raise such antibodies, there may be used as immunogen either the intact, soluble receptor or an immunogenic fragment thereof, produced in a microbial or mammalian cell host as described above or by standard peptide synthesis techniques. Regions of the EAA2a receptor particularly suitable for use as immunogenic fragments include those corresponding in sequence to an extracellular region of the receptor, or a portion of the extracellular region, such as peptides consisting of residues 1–527, including particularly residues 107–121 or 179–192 or 464–510, and peptides corresponding to regions between transmembrane domains Tm-2 and TM-3, such as a peptide consisting of residues 464–510. Peptides consisting of the C-terminal domain (residues 807–962) or a fragment thereof such as a peptide consisting of residues 927–942, may also be used for the raising of antibodies. Substantially the same regions of the human EAA2b and EAA2c receptors may also be used for production of antibodies against these receptors.

The raising of antibodies to the desired EAA2 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA2 receptor subunit, and selected regions thereof, may also be used, in accordance with another aspect of the present invention, as hybridization probes, for example to identify sequence-related genes resident in the human or other mammalian genomes (or cDNA libraries) or to locate the EAA2-encoding DNA in a specimen, such as brain tissue. This can be done using either the intact coding region, or a fragment thereof having radiolabelled e.g. $^{32}P$, nucleotides incorporated therein. To identify the EAA2-encoding DNA in a specimen, it is desirable to use either the full length cDNA coding therefor, or a fragment which is unique thereto. With reference to FIG. 1 and the nucleotide numbering appearing thereon, such nucleotide fragments include those corresponding in sequence to the following regions: 176–1580, 548–592, 1295–1376, 2844–2927, 3007–3120, 1856–1880, 1908–1929, 1998–2021, and 2298–2328. These sequences, and the intact gene itself, may also be used of course to clone EAA2-related genes by standard hybridization techniques.

EXAMPLE 1

Isolation of DNA coding for the human EAA2a receptor

As a first step in the isolation of DNA coding for a human EAA receptor, the published nucleotide sequences of rat GluR1 receptor, and chicken and frog kainate binding proteins were compared to identify spaced regions of homology, capable of serving as sites for primer binding, and PCR-based amplification. Oligonucleotide primers putatively capable of hybridizing with sequence-related regions in human cDNA, and having non-hybridizing flanks bearing HindIII restriction sites for subsequent cloning work, were then synthesized based on the published sequence of the rat GluR1 gene using conventional techniques of gene synthesis, to generate primers of the following sequence:

(SEQ ID NO:23)
5' GGGGTTTAAGCTTGAGCGTCGTCCTCTTCCTGGT 3'

(SEQ ID NO:24)
5' GGGGTTTAAGCTTGTGAAGAACCACCAGACGCCG 3'

Using human hippocampal cDNA as template (obtained as an EcoRI-based lambda gt10 library from Clontech Laboratories (Palo Alto, Calif., U.S.A.) the primers were then used in an attempt to amplify homologous sequences in the human cDNA, by application of the polymerase chain reaction technique. Reaction mixtures contained, in 100 ul, 100 ng of human hippocampal cDNA, 125 pmol of each primer and 2U Taq polymerase (in 10 mM Tris-HCl, pH9.0, 50 mM KCl, 1.5 mM MgCl$_2$, and with 0.2 mM of each deoxyribonucleotide species). There were then performed thirty cycles of 94° C./1 min; 58° C./1 min; 72° C./2 min, followed by a final cycle of 72° C./30 min.

There was generated an amplification product having an expected nucleotide length (239 bp). The product of amplification was then liberated from the gel and sub-cloned for sequencing into the HindIII site of phagemid vector pTZ19 (Pharmacia). The nucleotide sequence of the amplification product (without primers) is represented, retrospectively, from nucleotide #1867 to nucleotide #2037 inclusive (FIGS. 1(a)–1(c). A comparison of the sequence amplified from the human cDNA template with the corresponding region of the rat GluR gene on which the oligonucleotide primers were based revealed only about 60% identity, indicating that a fragment from an unrelated human gene had been identified.

To isolate cDNA coding for the entire human EAA2a receptor, a lambda gt10-based library of human hippocampal cDNA was probed using a PCR-generated, labelled (alpha-$^{32}$P-dCTP) version of the 239 bp amplification product. Of $10^6$ clones screened, probing identified 60 putative clones under the following high stringency hybridization conditions: 6× SSC, 50% formamide, 5% Denhardt's solution, 0.5% SDS, 100 Mg/ml denatured salmon sperm DNA. Hybridizations were carried out at 37° C. overnight, and filters were washed with 2× SSC containing 0.5% SDS at 25° C. for 5 minutes, followed by a 15 minute wash at 50° C. with 2× SSC containing 0.5% SDS. The final wash with 1× SSC containing 0.5% SDS at 50° C. for 15 minutes. Filters were exposed to X-ray film (Kodak) overnight.

Hybridization studies were performed in duplicate, and only those clones which hybridized well in both duplicates were selected for further analysis. Upon second round screening, 50 of the original 60 putative clones were selected. All 50 putative clones were plaque-purified, large scale DNA preps were made, and then DNA inserts liberated therefrom were subcloned into the EcoRI site of pTZ18 vectors, for sequence analysis. Sequencing revealed one clone harbouring, internally, a region with a nucleotide sequence similar to the sequence of the original 239 bp subclone. The entire sequence of the isolated clone (442 bp) was then determined. Retrospectively, this 442 bp sub-clone is represented from nucleotide 1776 to nucleotide 2217 inclusive FIGS. 1(a)–1(g).

Figure 3A:
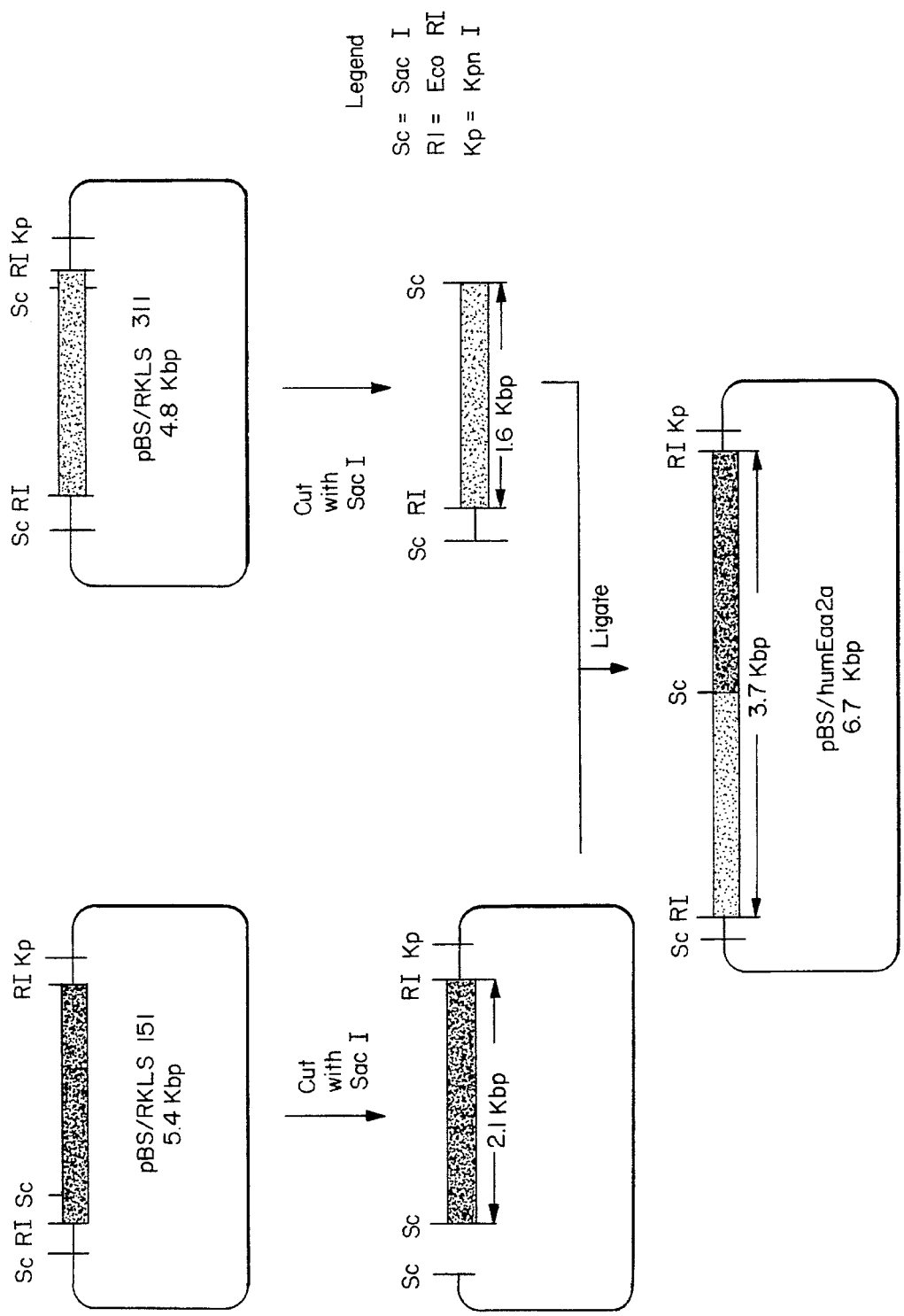
Figure 3B:
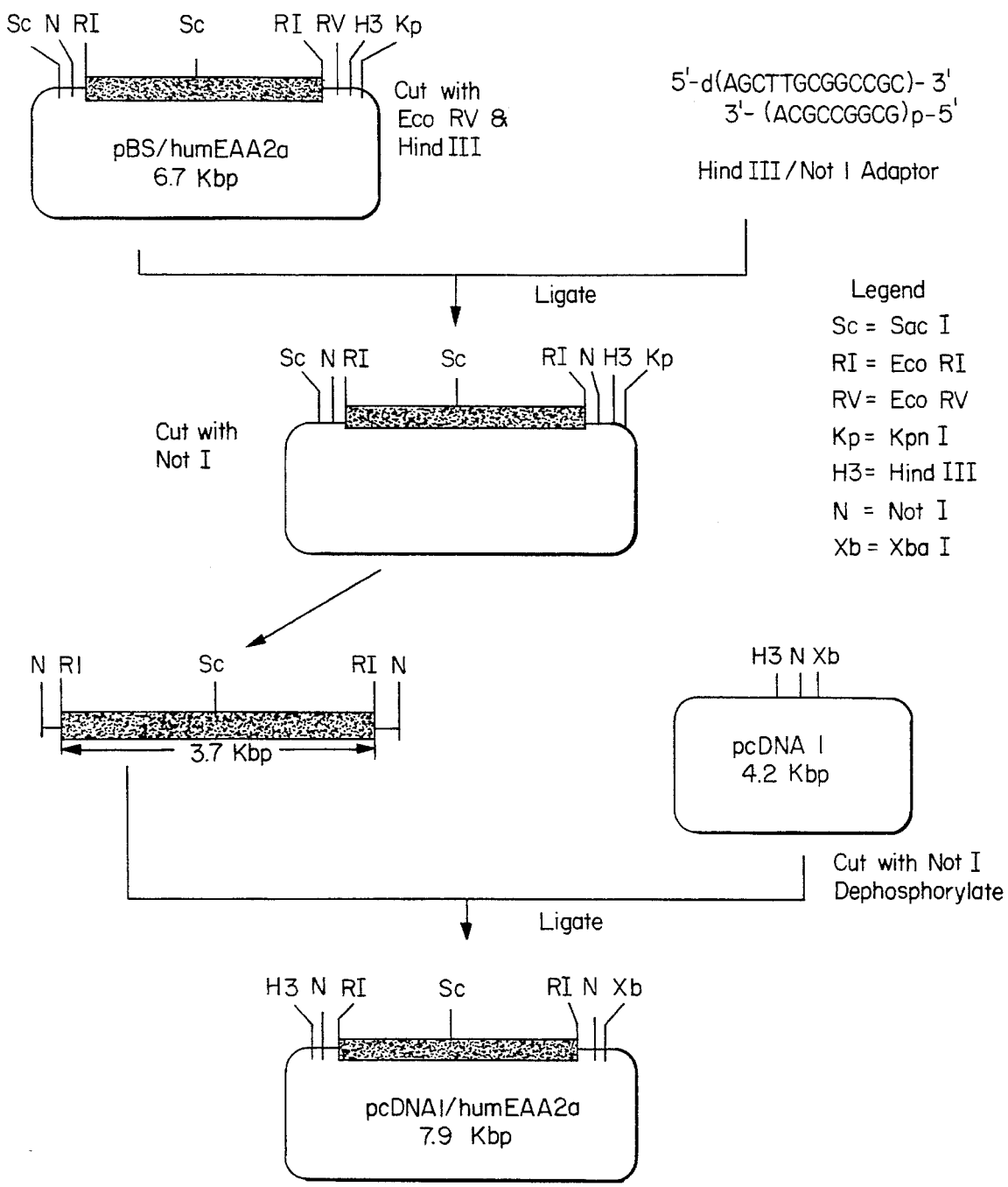

Since it was likely by analogy with the other receptor genes that the 442 bp was not full length, an alternative human hippocampal cDNA library constructed in a lambda phage system known commercially as lambda ZAP II was obtained (Stratagene Cloning Systems, La Jolla, Calif., U.S.A.) and screened using a PCR-generated, radiolabelled version of the 442 bp subclone. Screening of $10^6$ clones of this library by hybridization under the stringency conditions detailed above lead initially to the selection of 47 positive clones. For sequencing, phagemids carrying the inserts were excised, to generate insert-carrying variants of the phagemid vector known commercially as Bluescript-SK. Sequencing analysis identified two phagemid clones sharing a sequence overlap. One clone carrying a 1.8 kb EcoRI/EcoRI insert, and apparently representing a 5' region of the open reading frame, was designated pBS/RKLS311. The overlapping clone carrying a 2.4 kb EcoRI/EcoRI insert and appearing to represent the remaining 3' region of the open reading frame, was designated pBS/RKLS151. To construct the entire open reading frame, the strategy shown in FIGS. 3(a) and 3(g) was employed, to generate the phagemid pBS/HumEAA2a which carries the EAA2a-encoding DNA as a 3.7 kb EcoRI/EcoRI insert (recoverable intact as a 3.7 kb NotI/HindIII insert) in a 3.0 kb Bluescript-SK phagemid background. The entire sequence of the EcoRI insert is provided in FIGS. 1(a)–1(g).

The 6.7 kb phagemid pBS/humEAA2a was deposited, under the terms of the Budapest Treaty, with the American Type Culture Collection in Rockville, Md. USA on Aug. 21, 1991, and has been assigned accession number ATCC 75065.

EXAMPLE 2

Alternative strategy for obtaining EAA2a receptor-encoding DNA

Having herein provided the nucleotide sequence of EAA2a-encoding DNA, it will be appreciated that isolation thereof by the procedures just described is unnecessary, and can be replaced by application of automated techniques of gene synthesis and amplification. Using an appropriate cDNA library as template, for example a carefully prepared human hippocampal cDNA library, the polymerase chain reaction technique can be applied to amplify the desired cDNA product. While current PCR protocols are unlikely to enable direct amplification of the entire 3.7 kb gene, regional amplification to generate ligatable gene fragments is a feasible approach to gene construction.

With reference specifically to the EAA2a-encoding DNA, PCR-facilitated gene construction can proceed, for example, as illustrated in FIG. 2. More particularly, regions of the cloned cDNA template are amplified as fragments comprising on the order of several hundred nucleotides, using primers bearing non-hybridizing 5' flanks that constitute restriction sites useful in subsequent steps of gene assembly. In the example illustrated in FIG. 2, the gene is amplified as 4 individual fragments that can be ligated, because of the careful selection of restriction sites, in one step to form the entire EAA2a receptor-encoding DNA.

It will also be appreciated that automated techniques of gene synthesis can be applied, to provide gene fragments that by PCR can be amplified and subsequently ligated. Using current protocols, for example as described by Barnett et al in Nucl. Acids Res., 1990, 18(10):3094, fragments up to about 300 bases in length can be synthesized, and then amplified again using restriction site-tailed primers to facilitate assembly of the de novo synthesized gene regions.

EXAMPLE 3

Construction of cell lines producing the human EAA2a receptor

For transient expression in mammalian cells, cDNA coding for the human EAA2a receptor was incorporated into the mammalian expression vector pcDNA1, which is available commercially from Invitrogen Corporation (San Diego, Calif., USA; catalogue number V490-20). This is a multi-functional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1 like high copy plasmid origin. A polylinker is located appropriately downstream of the CMV promoter (and 3' of the T7 promoter).

For incorporation of the EAA2a receptor-encoding cDNA into an expression vector, the cDNA source phagemid pBS/humEAA2a was first modified to provide a NotI site 3' of the cDNA insert. This was achieved by restricting the phagemid with HindIII and EcoRV, and then inserting a HindIII/NotI adaptor sequence at the HindIII site followed by blunt end ligation to recircularize the phagemid, to yield pBS/humEAA2a-NotI. This modification permitted the full length cDNA insert to be released as a 3.7 kb NotI/NotI fragment, which was then incorporated at the NotI site in the pcDNAI polylinker. Sequencing across the NotI junction was performed, to confirm proper insert orientation in pcDNA1. The resulting plasmid, designated pcDNA1/humEAA2a, was then introduced for transient expression into a selected mammalian cell host, in this case the monkey-derived, fibroblast-like cells of the COS-1 lineage (available from the American Type Culture Collection, Rockville, Md. as ATCC CRL 1650).

For transient expression of the EAA2-encoding DNA, COS-1 cells were transfected with approximately 8 µg DNA (as pcDNA1/humEAA2a) per $10^6$ COS cells, by DEAE-mediated DNA transfection and treated with chloroquine according to the procedures described by Maniatis et al, supra. Briefly, COS-1 cells were plated at a density of $5 \times 10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 uM chloroquine 10% NuSerum, DNA (0.4 mg/ml) in DMEM/F12 medium. After incubation for 3 hours at 37° C., cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines were also prepared using two different cell types as host: CHO K1 and CHO Pro5. To construct these cell lines, cDNA coding for human EAA2a was incorporated into the NotI site of a 7.1 kb derivative of plasmid vector pcDNA1, which incorporates the neomycin gene under control of the Rous Sarcoma Virus LTR promoter and is designated pcDNA1/NEO (available also from Invitrogen Corporation, catalogue #V492-20). In a similar fashion, and again using a convenient NotI site for insertion, the receptor-encoding cDNA was inserted into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells were first seeded at a density of $5 \times 10^5$ in 10% FBS-supplemented MEM medium. After growth for 24 hours, fresh medium was added to the plates and three hours later, the cells were transfected using the calcium phosphate-DNA co-precipitation procedure (Maniatis et al, supra). Briefly, 3 Mg of DNA was mixed and incubated with buffered calcium solution for 10 minutes at room temperature. An equal volume of buffered phosphate solution was added and the suspension was incubated for 15 minutes at room temperature. Next, the incubated suspension was applied to the cells for 4 hours, removed and cells were shocked with medium containing 15% glycerol. Three minutes later, cells were washed with medium and incubated for 24 hours at normal growth conditions. Cells resistant to neomycin were selected in 10% FBS-supplemented alpha-MEM medium containing G418 (1 mg/ml). Individual colonies of G418-resistant cells were isolated about 2–3 weeks later, clonally selected and then propogated for assay purposes.

EXAMPLE 4

Ligand binding assays

Transfected cells in the frozen state were resuspended in ice-cold distilled water using a hand homogenizer and centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5° C.) and placed inside Spectrapor 7 (EDTA-treated, sulfur-free)dialysis tubing. The suspension was placed in 4 liters of ice cold 50 mM Tris-HCl (pH 7.55, 5° C.) and dialyzed for 16–24 hours at 5° C. in order to remove endogenous glutamate that would compete for binding. The tissue suspension was recovered from the tubing along with a small volume of buffer used to rinse the tubing. This resultant membrane preparation was used as tissue source for binding experiments described below. Proteins were determined using the Pierce Reagent with BSA as standard.

Binding assays were then performed, using an amount of COS-derived membrane equivalent to from 25–100 Mg as judged by protein determination and selected radiolabelled ligand. In particular, glutamate binding assays entailed formation of an incubation mixture consisting of 25–100 Mg of tissue protein, and [3,4-3H]L-glutamic acid (47.3 Ci/mmole, 10 nM final) in 50 mM Tris-HCl (pH 7.55, 5° C.) in 1 ml final volume. Non-specific binding was in the presence of 1 mM L-glutamate. Samples were incubated on ice for 60 minutes in plastic minivials. Bound and free ligand were separated by centrifugation for 10 minutes at 50,000 g (4° C.). Tissue pellets were washed superficially with 2×6 ml of ice cold incubation buffer. Pellets were solubilized and counted in 5 ml of Beckman Ready Protein Scintillation cocktail.

For kainate binding assays, incubation mixtures consisted of 25–100 μg tissue protein and [vinylidene-3H] kainic acid (58 Ci/mmole, 5 nM final) in the cold incubation buffer, 1 ml final volume. Non-specific binding was in the presence of 1 mM L-glutamate. Samples were incubated as for the glutamate binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Safe scintillation cocktail for counting.

AMPA-binding assays were also performed in substantially the same manner described above for kainate binding, but using as ligand D,L-alpha-[5-methyl-3H]amino-3-hydroxy-5-methylisoxazole-4-propionic acid (3H-AMPA, 27.6 Ci/mmole, 5 nM final) with 0.1M KSCN and 2.5 mM CaCl₂ in the 1 ml final volume.

Figure 5A:
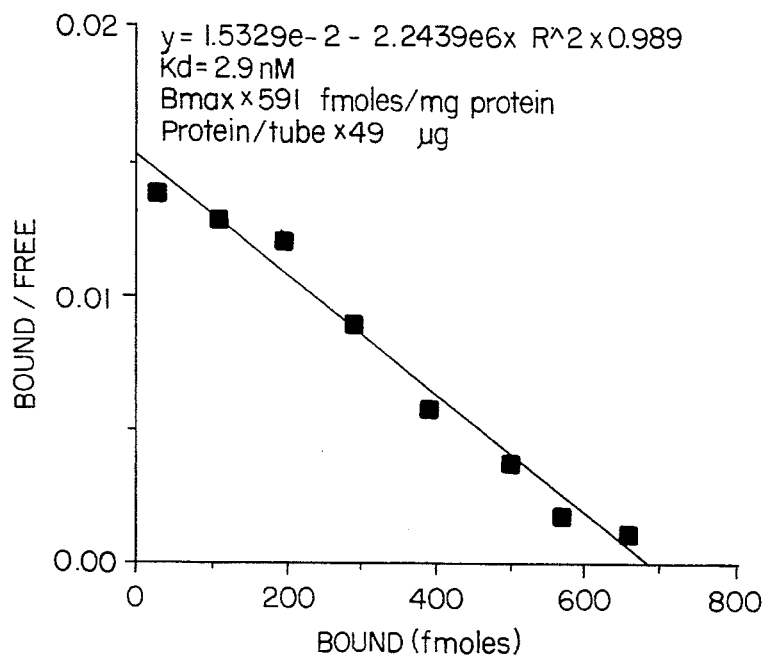
Figure 5B:
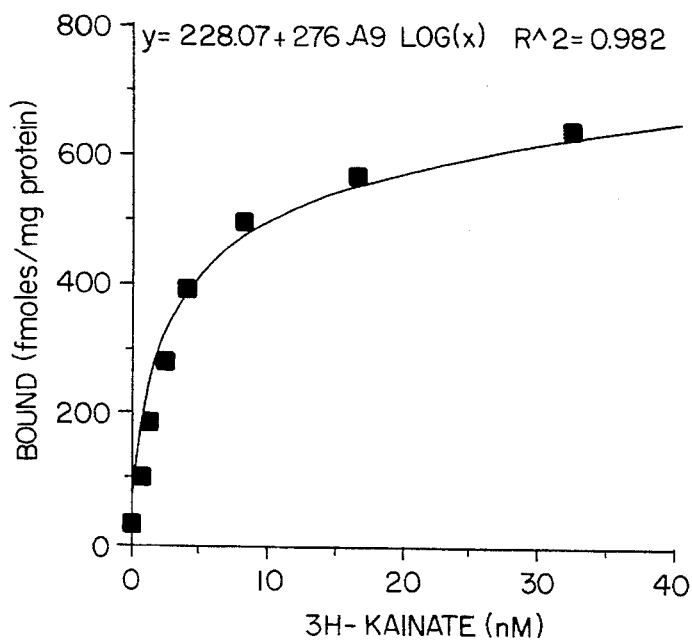

Assays performed in this manner revealed specific [3H]-kainate binding at 5 nM and [3H]-glutamate binding at 10 nM, labelled ligand. Scatchard analysis indicated that the recombinantly expressed human EAA2a receptor contained a single class of [3H]-labelled kainate binding sites with a dissocation constant (Kd) of 2.9 nM (FIGS. 5(a) and 5(b)), and a maximum binding (Bmax) of 691 fmol/mg protein. Mock transfected cells exhibited no specific binding of any of the ligands tested.

Figure 6:
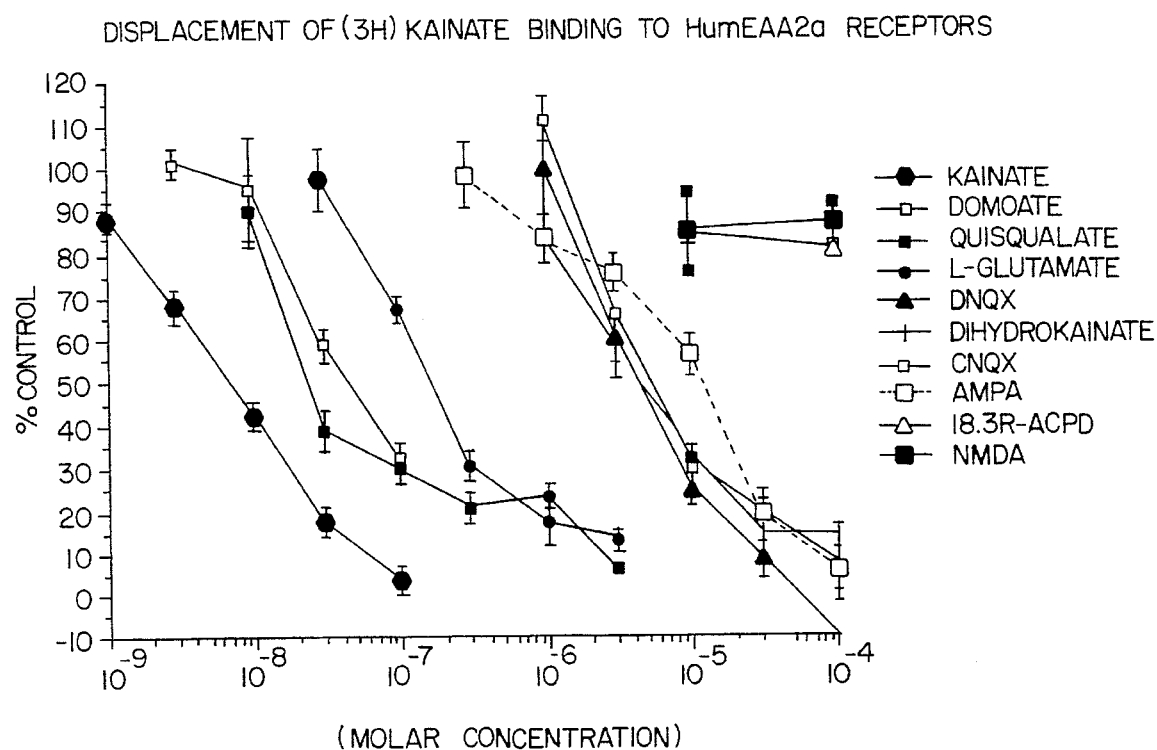

Additional assays were also performed, the results of which are shown in FIG. 6. Displacement of [3H]-labelled kainate binding with the noted selective ligands showed a rank order of potency of: kainate>domoate>quisqualate>glutamate>DNQX>dihydrokainate>CNQX>AMPA. No displacement of kainate was observed with NMDA or 1S,3R-ACPD at concentrations up to 100 μM.

The data obtained with the ligand-binding assays demonstrate clearly that the EAA2a receptor is binding kainate with high affinity. This activity, coupled with the fact that there is little or no demonstrable binding of either AMPA or NMDA clearly assigns the EAA2a receptor to be of the kainate type of EAA receptor. Furthermore, this binding profile, especially with the kainate binding being of the high affinity category (i.e. nanomolar range) indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA2a receptor gene in a pure form, capable of being expressed as a single, homogenous receptor species, therefore frees the ligand binding assay from the lack of precision introduced when complex, heterogeneous receptor preparations from human brains are used to attempt such characterizations.

EXAMPLE 5

Naturally occurring variants of the human EAA2a receptor

Figure 4C:
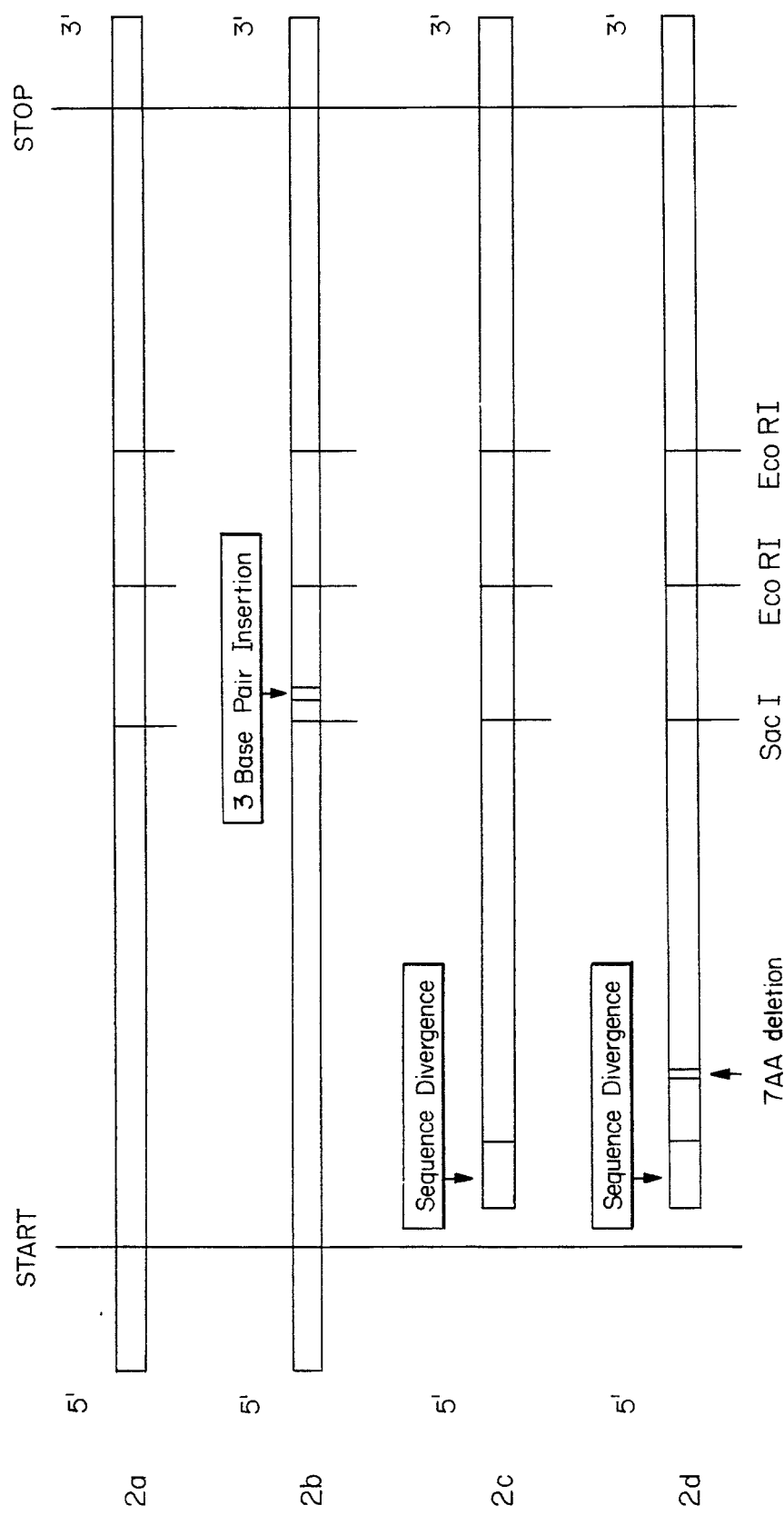

Using the same 442bp probe which lead to the successful identification of the human EAA2a receptor, two sequence-related variants thereof were also identified and isolated in substantially the same manner. As shown in FIGS. 4(a), 4(b) and 4(c); one variant designated EAA2b is nearly identical in all structural respects to the human EAA2a receptor, and differs only by the precise insertion in EAA2b of the glutamine-encoding triplet CAG, between nucleotide positions 1648 and 1649 of EAA2a. Like DNA coding for EAA2a, the EAA2b-encoding DNA was isolated from a cDNA library of human hippocampal DNA. To construct the full length cDNA containing the entire open reading frame, overlapping clones pBSRKLS311 (representing the 5'region) and pBS/RKLS511 (representing the 3'-region) were used in the same manner as described for humEAA2a. For binding studies, the isolated cDNA was tailored first to incorporate the 3' NotI site, and was then introduced for transient expression into cells of the COS-1 lineage after insertion into the vector pcDNA1 (transient expression) and into CHO K1 or CHO Pro5 cell after insertion into vectors pcDNA1/NEO or pRC/CMV all in the same manner as described above for human EAA2a. Ligand binding studies, while preliminary, indicate the same pattern of ligand binding affinity, and thus demonstrate that the EAA2b variant is also a human EAA receptor of the kainate-binding type.

A plasmid, designated pBS/humEAA2b, which carries a 3.7 kb NotI/HindIII cDNA insert coding for the human EAA2b receptor in a 3.0 kb Bluescript-SK background, has been deposited, under the terms of the Budapest Treaty, with the American Type Culture Collection in Rockville, Maryland USA on Aug. 21, 1991, under accession number ATCC 75066.

Isolation of an additional EAA2a variant, designated EAA2c, has demonstrated that expression of genes coding for human EAA receptors of the kainate type is not restricted to hippocampal tissue. More particularly, whereas both human EAA2a and human EAA2b were isolated after probing hippocampal cDNA libraries, the variant EAA2c was isolated using the same 442 bp probe from a library of human cerebellum cDNA, (available from Stratagene Cloning Systems). While sequencing of a minor 5' portion of the EAA2c coding region remains to be completed, it is clear, as shown in FIG. 4, that EAA2c differs from EAA2a only in a short region representing the signal peptide and at the extracellular N-terminus of the mature protein. Isolation of cDNA coding for the human EAA2c receptor, apart from being performed on the cerebellum library rather than the hippocampus library, was performed as described for human EAA2a.

We claim:

1. An isolated polynucleotide that codes for an EAA2a receptor having the amino acid sequence of 1–962 of SEQ ID NO:2; or an EAA2b receptor having the amino acid sequence of 1–962 of SEQ ID NO:2 including a glutamine insertion following the amino acid at position 473.

2. An isolated polynucleotide according to claim 1, consisting of DNA.

3. An isolated polynucleotide according to claim 1, that codes for the human EAA2a receptor.

4. An isolated polynucleotide according to claim 1, that codes for the human EAA2b receptor.

5. A polynucleotide as defined in claim 1, having a nucleic acid sequence as set out in SEQ ID NO:1.

6. A polynucleotide as defined in claim 1, having a nucleic acid sequence as set out in SEQ ID NO:1, including a glutamine codon inserted between positions 1650 and 1651 thereof.

7. A vector having incorporated therein a polynucleotide as defined in claim 1.

8. A vector according to claim 7, wherein said polynucleotide encodes the human EAA2a receptor.

9. A vector according to claim 8, wherein said vector is plasmid pBS/humEAA2a (ATCC 75065).

10. A vector according to claim 7, wherein said polynucleotide encodes the human EAA2b receptor.

11. A vector according to claim 10, wherein said vector is plasmid pBS/humEAA2b (ATCC 75066).

12. A cell that has been genetically engineered to produce a kainate-binding human EAA2 receptor, said cell having incorporated expressibly therein a polynucleotide as defined in claim 1.

13. A eukaryotic cell according to claim 12, wherein said heterologous DNA molecule codes for the human EAA2a receptor.

14. A membrane preparation derived from a cell as defined in claim 13.

15. A eukaryotic cell according to claim 12, wherein said heterologous DNA molecule codes for the human EAA2b receptor.

16. A membrane preparation derived from a cell as defined in claim 15.

17. A cell according to claim 12, wherein said cell is a mammalian cell.

18. A membrane preparation derived from a cell as defined in claim 12.

19. A cell as defined in claim 12 which is a eukaryotic cell.

20. An oligonucleotide probe capable of hybridizing under stringent conditions with a polynucleotide that codes for a human EAA2a receptor having an amino acid sequence of residues 1–962 of SEQ ID NO: 2, said probe being selected from the group of nucleotides consisting of 1–3695, 176–1580, 548–592, 1295–1376, 2844–2927, 3007–3120, 1856–1880, 1908–1929, 1998–2021 and 2298–2328 of SEQ ID NO: 1.

21. A probe as defined in claim 20, selected from the group of nucleotides consisting of 1–3695, 548–592, 1295–1376, 2844–2927, 3007–3120, 1856–1880, 1908–1929, 1998–2021 and 2298–2328 of SEQ ID NO:1.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
    ( A ) LENGTH: 3695 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: sig_peptide
    ( B ) LOCATION: 176..229

( i x ) FEATURE:
    ( A ) NAME/KEY: mat_peptide
    ( B ) LOCATION: 230..3118

( i x ) FEATURE:
    ( A ) NAME/KEY: CDS
    ( B ) LOCATION: 176..3118

( x i ) SEQUENCE DESCRIPTION: SEQ ID NO:1:

```
GAATTCCGGC CCTGTGGACT GCCCTCTCCC CCCGCCCAGC CCCACCACCA CCCAGCGCCA        60

GAGCCACCTC CCGCTGTCGG TCTGCGGGCC TCGAGGGAGC CCAGCCCTCC GTCCCACCAG       120

GATCCGTGGC GAGTGGGGGC CGCGGCAGCT GCGTCCCCAT GAGGAGGGGA GGAAG ATG       178
                                                             Met
                                                             -18

CCG GCT GAG CTG CTG CTG CTG CTG ATT GTT GCC TTC GCC AGC CCC AGC       226
Pro Ala Glu Leu Leu Leu Leu Leu Ile Val Ala Phe Ala Ser Pro Ser
    -15                 -10                  -5

TGC CAG GTG CTC TCA TCA CTG CGC ATG GCT GCA ATC CTG GAT GAT CAG       274
Cys Gln Val Leu Ser Ser Leu Arg Met Ala Ala Ile Leu Asp Asp Gln
      1             5                  10                 15

ACA GTG TGT GGC CGC GGT GAG CGT CTG GCC TTG GCC TTG GCC CGG GAG       322
Thr Val Cys Gly Arg Gly Glu Arg Leu Ala Leu Ala Leu Ala Arg Glu
                20              25                  30

CAG ATC AAC GGG ATC ATC GAG GTC CCA GCC AAG GCC CGA GTG GAA GTA       370
Gln Ile Asn Gly Ile Ile Glu Val Pro Ala Lys Ala Arg Val Glu Val
            35                  40                  45

GAC ATC TTT GAG CTG CAG CGG GAC AGC CAG TAC GAG ACC ACG GAC ACC       418
Asp Ile Phe Glu Leu Gln Arg Asp Ser Gln Tyr Glu Thr Thr Asp Thr
        50                  55                  60

ATG TGT CAG ATC TTA CCC AAA GGG GTT GTG TCT GTC CTT GGG CCC TCC       466
Met Cys Gln Ile Leu Pro Lys Gly Val Val Ser Val Leu Gly Pro Ser
    65                  70                  75

TCT AGC CCA GCA TCT GCC TCC ACC GTG AGC CAT ATC TGT GGA GAG AAG       514
Ser Ser Pro Ala Ser Ala Ser Thr Val Ser His Ile Cys Gly Glu Lys
80                  85                  90                  95

GAG ATC CCC CAC ATC AAG GTG GGT CCC GAG GAG ACA CCC CGC CTT CAG       562
Glu Ile Pro His Ile Lys Val Gly Pro Glu Glu Thr Pro Arg Leu Gln
                100                 105                 110

TAC CTT CGC TTC GCG TCT GTC AGC CTG TAC CCC AGT AAC GAG GAC GTC       610
Tyr Leu Arg Phe Ala Ser Val Ser Leu Tyr Pro Ser Asn Glu Asp Val
            115                 120                 125

AGC TTG GCG GTC TCC CGA ATC CTC AAG TCC TTC AAC TAC CCC TCG GCC       658
Ser Leu Ala Val Ser Arg Ile Leu Lys Ser Phe Asn Tyr Pro Ser Ala
                130                 135                 140
```

| | | | | | | | | | | | | | | | | |
|---|---|---|---|---|---|---|---|---|---|---|---|---|---|---|---|---|
| AGC | CTC | ATC | TGC | GCC | AAG | GCT | GAG | TGC | CTG | CTG | CGA | TTG | GAG | GAA | CTG | 706 |
| Ser | Leu | Ile | Cys | Ala | Lys | Ala | Glu | Cys | Leu | Leu | Arg | Leu | Glu | Glu | Leu | |
| | 145 | | | | 150 | | | | | 155 | | | | | | |
| GTG | CGT | GGC | TTC | CTC | ATC | TCC | AAG | GAG | ACG | CTG | TCA | GTG | AGG | ATG | TTG | 754 |
| Val | Arg | Gly | Phe | Leu | Ile | Ser | Lys | Glu | Thr | Leu | Ser | Val | Arg | Met | Leu | |
| 160 | | | | | 165 | | | | | 170 | | | | | 175 | |
| GAC | GAC | AGC | CGG | GAC | CCC | ACA | CCA | CTG | CTC | AAG | GAG | ATC | CGT | GAT | GAC | 802 |
| Asp | Asp | Ser | Arg | Asp | Pro | Thr | Pro | Leu | Leu | Lys | Glu | Ile | Arg | Asp | Asp | |
| | | | | 180 | | | | | 185 | | | | | 190 | | |
| AAG | GTG | TCC | ACC | ATC | ATC | ATC | GAC | GCC | AAC | GCC | TCC | ATC | TCC | CAC | CTC | 850 |
| Lys | Val | Ser | Thr | Ile | Ile | Ile | Asp | Ala | Asn | Ala | Ser | Ile | Ser | His | Leu | |
| | | | 195 | | | | | 200 | | | | | 205 | | | |
| ATC | CTC | CGT | AAG | GCC | TCG | GAA | CTG | GGA | ATG | ACC | TCA | GCG | TTT | TAC | AAG | 898 |
| Ile | Leu | Arg | Lys | Ala | Ser | Glu | Leu | Gly | Met | Thr | Ser | Ala | Phe | Tyr | Lys | |
| | | 210 | | | | | 215 | | | | | 220 | | | | |
| TAC | ATC | CTC | ACC | ACC | ATG | GAC | TTC | CCC | ATC | CTG | CAT | CTG | GAC | GGT | ATT | 946 |
| Tyr | Ile | Leu | Thr | Thr | Met | Asp | Phe | Pro | Ile | Leu | His | Leu | Asp | Gly | Ile | |
| | 225 | | | | | 230 | | | | | 235 | | | | | |
| GTG | GAG | GAC | TCC | TCC | AAC | ATC | CTG | GGC | TTC | TCC | ATG | TTC | AAC | ACG | TCC | 994 |
| Val | Glu | Asp | Ser | Ser | Asn | Ile | Leu | Gly | Phe | Ser | Met | Phe | Asn | Thr | Ser | |
| 240 | | | | | 245 | | | | | 250 | | | | | 255 | |
| CAC | CCC | TTC | TAC | CCT | GAG | TTT | GTC | CGC | AGC | CTC | AAC | ATG | TCC | TGG | AGG | 1042 |
| His | Pro | Phe | Tyr | Pro | Glu | Phe | Val | Arg | Ser | Leu | Asn | Met | Ser | Trp | Arg | |
| | | | | 260 | | | | | 265 | | | | | 270 | | |
| GAG | AAC | TGT | GAA | GCC | AGC | ACC | TAC | CTG | GGC | CCT | GCG | CTG | TCA | GCC | GCC | 1090 |
| Glu | Asn | Cys | Glu | Ala | Ser | Thr | Tyr | Leu | Gly | Pro | Ala | Leu | Ser | Ala | Ala | |
| | | | 275 | | | | | 280 | | | | | 285 | | | |
| CTG | ATG | TTT | GAC | GCC | GTG | CAC | GTG | GTG | GTG | AGC | GCT | GTC | CGA | GAG | CTG | 1138 |
| Leu | Met | Phe | Asp | Ala | Val | His | Val | Val | Val | Ser | Ala | Val | Arg | Glu | Leu | |
| | | 290 | | | | | 295 | | | | | 300 | | | | |
| AAC | CGC | AGC | CAG | GAG | ATC | GGT | GTG | AAG | CCT | CTG | GCC | TGT | ACA | TCG | GCC | 1186 |
| Asn | Arg | Ser | Gln | Glu | Ile | Gly | Val | Lys | Pro | Leu | Ala | Cys | Thr | Ser | Ala | |
| | 305 | | | | | 310 | | | | | 315 | | | | | |
| AAC | ATT | TGG | CCC | CAC | GGG | ACC | AGC | CTC | ATG | AAC | TAC | CTG | CGC | ATG | GTA | 1234 |
| Asn | Ile | Trp | Pro | His | Gly | Thr | Ser | Leu | Met | Asn | Tyr | Leu | Arg | Met | Val | |
| 320 | | | | | 325 | | | | | 330 | | | | | 335 | |
| GAG | TAT | GAT | GGG | CTG | ACC | GGG | CGG | GTC | GAG | TTC | AAC | AGC | AAA | GGG | CAG | 1282 |
| Glu | Tyr | Asp | Gly | Leu | Thr | Gly | Arg | Val | Glu | Phe | Asn | Ser | Lys | Gly | Gln | |
| | | | | 340 | | | | | 345 | | | | | 350 | | |
| AGA | ACC | AAC | TAC | ACC | CTG | CGC | ATC | CTA | GAA | AAG | TCC | CGG | CAG | GGC | CAC | 1330 |
| Arg | Thr | Asn | Tyr | Thr | Leu | Arg | Ile | Leu | Glu | Lys | Ser | Arg | Gln | Gly | His | |
| | | | 355 | | | | | 360 | | | | | 365 | | | |
| CGT | GAG | ATT | GGG | GTG | TGG | TAC | TCT | AAC | CGC | ACC | CTG | GCC | ATG | AAT | GCC | 1378 |
| Arg | Glu | Ile | Gly | Val | Trp | Tyr | Ser | Asn | Arg | Thr | Leu | Ala | Met | Asn | Ala | |
| | | 370 | | | | | 375 | | | | | 380 | | | | |
| ACC | ACC | CTG | GAC | ATC | AAC | CTG | TCG | CAG | ACA | CTG | GCC | AAC | AAG | ACC | CTG | 1426 |
| Thr | Thr | Leu | Asp | Ile | Asn | Leu | Ser | Gln | Thr | Leu | Ala | Asn | Lys | Thr | Leu | |
| | 385 | | | | | 390 | | | | | 395 | | | | | |
| GTG | GTC | ACA | ACC | ATC | CTG | GAG | AAC | CCA | TAC | GTC | ATG | CGC | CGG | CCC | AAC | 1474 |
| Val | Val | Thr | Thr | Ile | Leu | Glu | Asn | Pro | Tyr | Val | Met | Arg | Arg | Pro | Asn | |
| 400 | | | | | 405 | | | | | 410 | | | | | 415 | |
| TTC | CAG | GGC | CTG | TCG | GGG | AAC | GAA | CGC | TTC | GAG | GGC | TTC | TGC | GTG | GAC | 1522 |
| Phe | Gln | Gly | Leu | Ser | Gly | Asn | Glu | Arg | Phe | Glu | Gly | Phe | Cys | Val | Asp | |
| | | | | 420 | | | | | 425 | | | | | 430 | | |
| ATG | CTG | CGG | GAG | CTG | GCC | GAG | CTG | CTG | CCG | TTC | CCG | TAC | CGC | CTG | CGG | 1570 |
| Met | Leu | Arg | Glu | Leu | Ala | Glu | Leu | Leu | Pro | Phe | Pro | Tyr | Arg | Leu | Arg | |
| | | | 435 | | | | | 440 | | | | | 445 | | | |
| TTG | GTG | GAG | GAT | GGG | CTG | TAC | GGG | GCG | CCC | GAG | CCC | AAC | GGC | TCC | TGG | 1618 |
| Leu | Val | Glu | Asp | Gly | Leu | Tyr | Gly | Ala | Pro | Glu | Pro | Asn | Gly | Ser | Trp | |
| | | 450 | | | | | 455 | | | | | 460 | | | | |

| | | | | | | | | | | | | | | | | |
|---|---|---|---|---|---|---|---|---|---|---|---|---|---|---|---|---|
| ACG | GGC | ATG | GTT | GGC | GAG | CTC | ATC | AAC | CGG | AAG | GCA | GAC | CTG | GCT | GTG | 1666 |
| Thr | Gly | Met | Val | Gly | Glu | Leu | Ile | Asn | Arg | Lys | Ala | Asp | Leu | Ala | Val | |
| | 465 | | | | 470 | | | | | 475 | | | | | | |
| GCC | GCC | TTC | ACC | ATC | ACA | GCT | GAG | CGG | GAG | AAG | GTC | ATC | GAC | TTT | TCC | 1714 |
| Ala | Ala | Phe | Thr | Ile | Thr | Ala | Glu | Arg | Glu | Lys | Val | Ile | Asp | Phe | Ser | |
| 480 | | | | | 485 | | | | | 490 | | | | | 495 | |
| AAG | CCC | TTT | ATG | ACC | CTG | GGG | ATC | AGC | ATC | CTC | TAC | CGA | GTG | CAC | ATG | 1762 |
| Lys | Pro | Phe | Met | Thr | Leu | Gly | Ile | Ser | Ile | Leu | Tyr | Arg | Val | His | Met | |
| | | | | 500 | | | | | 505 | | | | | 510 | | |
| GGC | CGC | AAG | CCT | GGC | TAC | TTC | TCC | TTC | CTG | GAC | CCC | TTC | TCC | CCT | GCT | 1810 |
| Gly | Arg | Lys | Pro | Gly | Tyr | Phe | Ser | Phe | Leu | Asp | Pro | Phe | Ser | Pro | Ala | |
| | | | 515 | | | | | 520 | | | | | 525 | | | |
| GTG | TGG | CTC | TTC | ATG | CTT | CTT | GCC | TAC | CTG | GCT | GTC | AGC | TGC | GTC | CTG | 1858 |
| Val | Trp | Leu | Phe | Met | Leu | Leu | Ala | Tyr | Leu | Ala | Val | Ser | Cys | Val | Leu | |
| | | | 530 | | | | | 535 | | | | | 540 | | | |
| TTT | CTG | GCT | GCC | AGG | CTG | AGC | CCC | TAT | GAG | TGG | TAT | AAC | CCA | CAC | CCA | 1906 |
| Phe | Leu | Ala | Ala | Arg | Leu | Ser | Pro | Tyr | Glu | Trp | Tyr | Asn | Pro | His | Pro | |
| | 545 | | | | | 550 | | | | | 555 | | | | | |
| TGC | CTG | CGG | GCA | CGC | CCC | CAC | ATC | CTG | GAG | AAC | CAG | TAC | ACG | CTG | GGC | 1954 |
| Cys | Leu | Arg | Ala | Arg | Pro | His | Ile | Leu | Glu | Asn | Gln | Tyr | Thr | Leu | Gly | |
| 560 | | | | | 565 | | | | | 570 | | | | | 575 | |
| AAC | AGC | CTG | TGG | TTT | CCC | GTG | GGG | GGC | TTC | ATG | CAG | CAG | GGC | TCG | GAG | 2002 |
| Asn | Ser | Leu | Trp | Phe | Pro | Val | Gly | Gly | Phe | Met | Gln | Gln | Gly | Ser | Glu | |
| | | | | 580 | | | | | 585 | | | | | 590 | | |
| ATC | ATG | CCC | CGG | GCG | CTG | TCC | ACG | CGC | TGT | GTC | AGC | GGA | GTC | TGG | TGG | 2050 |
| Ile | Met | Pro | Arg | Ala | Leu | Ser | Thr | Arg | Cys | Val | Ser | Gly | Val | Trp | Trp | |
| | | | 595 | | | | | 600 | | | | | 605 | | | |
| GCC | TTC | ACC | TTG | ATC | ATC | ATC | TCC | TCC | TAC | ACG | GCC | AAC | CTG | GCC | GCC | 2098 |
| Ala | Phe | Thr | Leu | Ile | Ile | Ile | Ser | Ser | Tyr | Thr | Ala | Asn | Leu | Ala | Ala | |
| | | 610 | | | | | 615 | | | | | 620 | | | | |
| TTC | CTC | ACC | GTG | CAG | CGC | ATG | GAG | GTG | CCT | GTG | GAG | TCG | GCC | GAT | GAC | 2146 |
| Phe | Leu | Thr | Val | Gln | Arg | Met | Glu | Val | Pro | Val | Glu | Ser | Ala | Asp | Asp | |
| | 625 | | | | | 630 | | | | | 635 | | | | | |
| CTG | GCA | GAT | CAG | ACC | AAC | ATC | GAG | TAT | GGC | ACC | ATC | CAC | GCC | GGC | TCC | 2194 |
| Leu | Ala | Asp | Gln | Thr | Asn | Ile | Glu | Tyr | Gly | Thr | Ile | His | Ala | Gly | Ser | |
| 640 | | | | | 645 | | | | | 650 | | | | | 655 | |
| ACC | ATG | ACC | TTC | TTC | CAG | AAT | TCA | CGG | TAC | CAA | ACG | TAC | CAG | CGC | ATG | 2242 |
| Thr | Met | Thr | Phe | Phe | Gln | Asn | Ser | Arg | Tyr | Gln | Thr | Tyr | Gln | Arg | Met | |
| | | | | 660 | | | | | 665 | | | | | 670 | | |
| TGG | AAC | TAC | ATG | CAG | TCG | AAG | CAG | CCC | AGC | GTG | TTC | GTC | AAG | AGC | ACA | 2290 |
| Trp | Asn | Tyr | Met | Gln | Ser | Lys | Gln | Pro | Ser | Val | Phe | Val | Lys | Ser | Thr | |
| | | | 675 | | | | | 680 | | | | | 685 | | | |
| GAA | GAG | GGC | ATT | GCC | GCC | GTC | CTC | AAC | TCC | CGC | TAC | GCC | TTC | CTG | CTC | 2338 |
| Glu | Glu | Gly | Ile | Ala | Ala | Val | Leu | Asn | Ser | Arg | Tyr | Ala | Phe | Leu | Leu | |
| | | 690 | | | | | 695 | | | | | 700 | | | | |
| GAG | TCC | ACC | ATG | AAC | GAA | TAC | CAC | CGG | CGC | CTC | AAC | TGC | AAC | CTC | ACC | 2386 |
| Glu | Ser | Thr | Met | Asn | Glu | Tyr | His | Arg | Arg | Leu | Asn | Cys | Asn | Leu | Thr | |
| | 705 | | | | | 710 | | | | | 715 | | | | | |
| CAG | ATC | GGG | GGA | CTC | CTC | GAC | ACC | AAG | GGC | TAC | GGC | ATT | GGC | ATG | CCG | 2434 |
| Gln | Ile | Gly | Gly | Leu | Leu | Asp | Thr | Lys | Gly | Tyr | Gly | Ile | Gly | Met | Pro | |
| 720 | | | | | 725 | | | | | 730 | | | | | 735 | |
| CTG | GGC | TCC | CCG | TTC | CGG | GAT | GAG | ATC | ACA | CTG | GCC | ATC | CTG | CAG | CTT | 2482 |
| Leu | Gly | Ser | Pro | Phe | Arg | Asp | Glu | Ile | Thr | Leu | Ala | Ile | Leu | Gln | Leu | |
| | | | | 740 | | | | | 745 | | | | | 750 | | |
| CAG | GAG | AAC | AAC | CGG | CTG | GAG | ATC | CTG | AAG | CGC | AAG | TGG | TGG | GAG | GGG | 2530 |
| Gln | Glu | Asn | Asn | Arg | Leu | Glu | Ile | Leu | Lys | Arg | Lys | Trp | Trp | Glu | Gly | |
| | | | 755 | | | | | 760 | | | | | 765 | | | |
| GGC | CGG | TGC | CCC | AAG | GAG | GAG | GAC | CAT | CGA | GCT | AAA | GGT | TTG | GGC | ATG | 2578 |
| Gly | Arg | Cys | Pro | Lys | Glu | Glu | Asp | His | Arg | Ala | Lys | Gly | Leu | Gly | Met | |
| | | 770 | | | | | 775 | | | | | 780 | | | | |

| | | | | | | | | | | | | | | | | |
|---|---|---|---|---|---|---|---|---|---|---|---|---|---|---|---|---|
| GAG | AAC | ATT | GGT | GGC | ATT | TTT | ATC | GTG | CTC | ATC | TGT | GGC | CTC | ATC | ATT | 2626 |
| Glu | Asn | Ile | Gly | Gly | Ile | Phe | Ile | Val | Leu | Ile | Cys | Gly | Leu | Ile | Ile | |
| | 785 | | | | 790 | | | | | | 795 | | | | | |
| GCT | GTC | TTC | GTG | GCG | GTC | ATG | GAA | TTC | ATA | TGG | TCC | ACA | CGG | AGG | TCA | 2674 |
| Ala | Val | Phe | Val | Ala | Val | Met | Glu | Phe | Ile | Trp | Ser | Thr | Arg | Arg | Ser | |
| 800 | | | | | 805 | | | | | 810 | | | | | 815 | |
| GCT | GAG | TCC | GAG | GAG | GTG | TCG | GTG | TGC | CAG | GAG | ATG | CTG | CAG | GAG | CTG | 2722 |
| Ala | Glu | Ser | Glu | Glu | Val | Ser | Val | Cys | Gln | Glu | Met | Leu | Gln | Glu | Leu | |
| | | | | 820 | | | | | 825 | | | | | 830 | | |
| CGC | CAC | GCC | GTT | TCT | TGC | CGC | AAG | ACG | TCG | CGT | TCC | CGC | CGG | CGC | CGA | 2770 |
| Arg | His | Ala | Val | Ser | Cys | Arg | Lys | Thr | Ser | Arg | Ser | Arg | Arg | Arg | Arg | |
| | | | 835 | | | | | 840 | | | | | 845 | | | |
| CGC | CCG | GGC | GGC | CCG | AGC | CGG | GCC | CTG | CTG | TCA | CTG | CGC | GCG | GTC | CGC | 2818 |
| Arg | Pro | Gly | Gly | Pro | Ser | Arg | Ala | Leu | Leu | Ser | Leu | Arg | Ala | Val | Arg | |
| | | 850 | | | | | 855 | | | | | 860 | | | | |
| GAG | ATG | CGC | CTC | AGC | AAC | GGC | AAG | CTC | TAC | TCG | GCC | GGC | GCG | GGC | GGG | 2866 |
| Glu | Met | Arg | Leu | Ser | Asn | Gly | Lys | Leu | Tyr | Ser | Ala | Gly | Ala | Gly | Gly | |
| | 865 | | | | | 870 | | | | | 875 | | | | | |
| GAT | GCG | GGC | AGC | GCG | CAC | GGG | GGC | CCG | CAG | CGC | CTC | CTG | GAC | GAC | CCG | 2914 |
| Asp | Ala | Gly | Ser | Ala | His | Gly | Gly | Pro | Gln | Arg | Leu | Leu | Asp | Asp | Pro | |
| 880 | | | | | 885 | | | | | 890 | | | | | 895 | |
| GGG | CCC | CCC | AGC | GGA | GCC | CGA | CCC | GCC | GCC | CCC | ACC | CCC | TGC | ACC | CAC | 2962 |
| Gly | Pro | Pro | Ser | Gly | Ala | Arg | Pro | Ala | Ala | Pro | Thr | Pro | Cys | Thr | His | |
| | | | | 900 | | | | | 905 | | | | | 910 | | |
| GTG | CGC | GTC | TGC | CAG | GAG | TGC | CGG | CGC | ATC | CAG | GCG | CTG | CGG | GCC | TCG | 3010 |
| Val | Arg | Val | Cys | Gln | Glu | Cys | Arg | Arg | Ile | Gln | Ala | Leu | Arg | Ala | Ser | |
| | | | 915 | | | | | 920 | | | | | 925 | | | |
| GGG | GCC | GGC | GCG | CCT | CCG | CGT | GGC | CTG | GGC | GTC | CCC | GCC | GAA | GCC | ACC | 3058 |
| Gly | Ala | Gly | Ala | Pro | Pro | Arg | Gly | Leu | Gly | Val | Pro | Ala | Glu | Ala | Thr | |
| | | 930 | | | | | 935 | | | | | 940 | | | | |
| AGC | CCG | CCC | CGG | CCG | CGG | CCT | GGC | CCC | GCC | GGC | CCC | CGG | GAG | CTG | GCG | 3106 |
| Ser | Pro | Pro | Arg | Pro | Arg | Pro | Gly | Pro | Ala | Gly | Pro | Arg | Glu | Leu | Ala | |
| | 945 | | | | | 950 | | | | | 955 | | | | | |
| GAG | CAC | GAG | TGACCACGGG | CGGGGCTGTG | CGGGCGCCCG | GACTGACCGA | | | | | | | | | | 3155 |
| Glu | His | Glu | | | | | | | | | | | | | | |
| 960 | | | | | | | | | | | | | | | | |

| | | | | | |
|---|---|---|---|---|---|
| AGGGACGGGG | CCCGCCCCAG | GCCCCAGCAG | TCTCCGCTCC | CGCAGCGGGC | GCGGGACAGG | 3215 |
| ACTTGTGCGC | CGGCGCCCCG | GACGCCGCGA | TTTTGCCTTT | GGTTCCCCGC | GAAGTCCGAG | 3275 |
| GCCTGGCTCT | GGAGCCCGCC | TGCGCCCCCC | AGTGGACTCG | CGAGAGGGTG | CCGCGGGCGA | 3335 |
| GAAGGGCGCA | GGAACCGAGG | ACTCCAGGGG | CTGGGGACTT | CGGGGCGGC | TCTGGGAAGC | 3395 |
| GGAAAGCAGT | CAGCGGAGAG | GACCCCATTC | TGGGACTGCT | CAGGCTCCCC | AAGACTTGAC | 3455 |
| GCAGCCCCCC | ACGCTTCTGA | GGTGGGGAGG | GCCTCTGGAC | AGATGGGTGT | CCCCTGGTGC | 3515 |
| CCCTCCACTC | TTTCTCTTCCT | CTCTTTTTG | GGGGAGAAA | CCTCGGAATT | TCTATGAGAC | 3575 |
| CTCCCCCAGG | GAGGGGGTCA | GTTGGGCCCC | CATCCCTCCC | CTTGCCACAT | CGCAGCCCCT | 3635 |
| GTTGGAATAA | AAAAAAGAAC | AAAAGGGGAA | AAAAAAAAA | AAAAAAAAA | AAAGGAATTC | 3695 |

( 2 ) INFORMATION FOR SEQ ID NO:2:

( i ) SEQUENCE CHARACTERISTICS:
        ( A ) LENGTH: 980 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Pro | Ala | Glu | Leu | Leu | Leu | Leu | Leu | Ile | Val | Ala | Phe | Ala | Ser | Pro |
| -18 | | | -15 | | | | | -10 | | | | | -5 | | |

| | | | | | | | | | | | | | |
|---|---|---|---|---|---|---|---|---|---|---|---|---|---|
| Ser | Cys | Gln | Val | Leu | Ser | Ser | Leu | Arg | Met | Ala | Ala | Ile | Leu | Asp | Asp |
| | | 1 | | | | 5 | | | | | 10 | | | | |
| Gln | Thr | Val | Cys | Gly | Arg | Gly | Glu | Arg | Leu | Ala | Leu | Ala | Leu | Ala | Arg |
| 15 | | | | | 20 | | | | | 25 | | | | | 30 |
| Glu | Gln | Ile | Asn | Gly | Ile | Ile | Glu | Val | Pro | Ala | Lys | Ala | Arg | Val | Glu |
| | | | | 35 | | | | | 40 | | | | | 45 | |
| Val | Asp | Ile | Phe | Glu | Leu | Gln | Arg | Asp | Ser | Gln | Tyr | Glu | Thr | Thr | Asp |
| | | | 50 | | | | | 55 | | | | | 60 | | |
| Thr | Met | Cys | Gln | Ile | Leu | Pro | Lys | Gly | Val | Val | Ser | Val | Leu | Gly | Pro |
| | | 65 | | | | | 70 | | | | | 75 | | | |
| Ser | Ser | Ser | Pro | Ala | Ser | Ala | Ser | Thr | Val | Ser | His | Ile | Cys | Gly | Glu |
| | | 80 | | | | 85 | | | | | 90 | | | | |
| Lys | Glu | Ile | Pro | His | Ile | Lys | Val | Gly | Pro | Glu | Glu | Thr | Pro | Arg | Leu |
| 95 | | | | | 100 | | | | | 105 | | | | | 110 |
| Gln | Tyr | Leu | Arg | Phe | Ala | Ser | Val | Ser | Leu | Tyr | Pro | Ser | Asn | Glu | Asp |
| | | | | 115 | | | | | 120 | | | | | 125 | |
| Val | Ser | Leu | Ala | Val | Ser | Arg | Ile | Leu | Lys | Ser | Phe | Asn | Tyr | Pro | Ser |
| | | | 130 | | | | | 135 | | | | | 140 | | |
| Ala | Ser | Leu | Ile | Cys | Ala | Lys | Ala | Glu | Cys | Leu | Leu | Arg | Leu | Glu | Glu |
| | | | 145 | | | | | 150 | | | | | 155 | | |
| Leu | Val | Arg | Gly | Phe | Leu | Ile | Ser | Lys | Glu | Thr | Leu | Ser | Val | Arg | Met |
| | | 160 | | | | | 165 | | | | | 170 | | | |
| Leu | Asp | Asp | Ser | Arg | Asp | Pro | Thr | Pro | Leu | Leu | Lys | Glu | Ile | Arg | Asp |
| 175 | | | | | 180 | | | | | 185 | | | | | 190 |
| Asp | Lys | Val | Ser | Thr | Ile | Ile | Ile | Asp | Ala | Asn | Ala | Ser | Ile | Ser | His |
| | | | | 195 | | | | | 200 | | | | | 205 | |
| Leu | Ile | Leu | Arg | Lys | Ala | Ser | Glu | Leu | Gly | Met | Thr | Ser | Ala | Phe | Tyr |
| | | | 210 | | | | | 215 | | | | | 220 | | |
| Lys | Tyr | Ile | Leu | Thr | Thr | Met | Asp | Phe | Pro | Ile | Leu | His | Leu | Asp | Gly |
| | | 225 | | | | | 230 | | | | | 235 | | | |
| Ile | Val | Glu | Asp | Ser | Ser | Asn | Ile | Leu | Gly | Phe | Ser | Met | Phe | Asn | Thr |
| | | 240 | | | | 245 | | | | | 250 | | | | |
| Ser | His | Pro | Phe | Tyr | Pro | Glu | Phe | Val | Arg | Ser | Leu | Asn | Met | Ser | Trp |
| 255 | | | | | 260 | | | | | 265 | | | | | 270 |
| Arg | Glu | Asn | Cys | Glu | Ala | Ser | Thr | Tyr | Leu | Gly | Pro | Ala | Leu | Ser | Ala |
| | | | | 275 | | | | | 280 | | | | | 285 | |
| Ala | Leu | Met | Phe | Asp | Ala | Val | His | Val | Val | Ser | Ala | Val | Arg | Glu |
| | | | 290 | | | | | 295 | | | | | 300 | | |
| Leu | Asn | Arg | Ser | Gln | Glu | Ile | Gly | Val | Lys | Pro | Leu | Ala | Cys | Thr | Ser |
| | | 305 | | | | | 310 | | | | | 315 | | | |
| Ala | Asn | Ile | Trp | Pro | His | Gly | Thr | Ser | Leu | Met | Asn | Tyr | Leu | Arg | Met |
| | 320 | | | | | 325 | | | | | 330 | | | | |
| Val | Glu | Tyr | Asp | Gly | Leu | Thr | Gly | Arg | Val | Glu | Phe | Asn | Ser | Lys | Gly |
| 335 | | | | | 340 | | | | | 345 | | | | | 350 |
| Gln | Arg | Thr | Asn | Tyr | Thr | Leu | Arg | Ile | Leu | Glu | Lys | Ser | Arg | Gln | Gly |
| | | | | 355 | | | | | 360 | | | | | 365 | |
| His | Arg | Glu | Ile | Gly | Val | Trp | Tyr | Ser | Asn | Arg | Thr | Leu | Ala | Met | Asn |
| | | | 370 | | | | | 375 | | | | | 380 | | |
| Ala | Thr | Thr | Leu | Asp | Ile | Asn | Leu | Ser | Gln | Thr | Leu | Ala | Asn | Lys | Thr |
| | | 385 | | | | | 390 | | | | | 395 | | | |
| Leu | Val | Val | Thr | Thr | Ile | Leu | Glu | Asn | Pro | Tyr | Val | Met | Arg | Arg | Pro |
| | 400 | | | | | 405 | | | | | 410 | | | | |
| Asn | Phe | Gln | Gly | Leu | Ser | Gly | Asn | Glu | Arg | Phe | Glu | Gly | Phe | Cys | Val |

|     |     |     |     |     |     |     |     |     |     |     |     |     |     |     |
|-----|-----|-----|-----|-----|-----|-----|-----|-----|-----|-----|-----|-----|-----|-----|
| | | | 415 | | | | 420 | | | | 425 | | | 430 |
| Asp | Met | Leu | Arg | Glu | Leu | Ala | Glu | Leu | Leu | Pro | Phe | Pro | Tyr | Arg | Leu |
| | | | | 435 | | | | 440 | | | | | 445 | |
| Arg | Leu | Val | Glu | Asp | Gly | Leu | Tyr | Gly | Ala | Pro | Glu | Pro | Asn | Gly | Ser |
| | | | 450 | | | | 455 | | | | 460 | | | |
| Trp | Thr | Gly | Met | Val | Gly | Glu | Leu | Ile | Asn | Arg | Lys | Ala | Asp | Leu | Ala |
| | | 465 | | | | 470 | | | | 475 | | | | |
| Val | Ala | Ala | Phe | Thr | Ile | Thr | Ala | Glu | Arg | Glu | Lys | Val | Ile | Asp | Phe |
| | 480 | | | | 485 | | | | 490 | | | | | |
| Ser | Lys | Pro | Phe | Met | Thr | Leu | Gly | Ile | Ser | Ile | Leu | Tyr | Arg | Val | His |
| 495 | | | | 500 | | | | 505 | | | | | | 510 |
| Met | Gly | Arg | Lys | Pro | Gly | Tyr | Phe | Ser | Phe | Leu | Asp | Pro | Phe | Ser | Pro |
| | | | 515 | | | | 520 | | | | 525 | | | |
| Ala | Val | Trp | Leu | Phe | Met | Leu | Leu | Ala | Tyr | Leu | Ala | Val | Ser | Cys | Val |
| | | | 530 | | | | 535 | | | | 540 | | | |
| Leu | Phe | Leu | Ala | Ala | Arg | Leu | Ser | Pro | Tyr | Glu | Trp | Tyr | Asn | Pro | His |
| | | 545 | | | | 550 | | | | 555 | | | | |
| Pro | Cys | Leu | Arg | Ala | Arg | Pro | His | Ile | Leu | Glu | Asn | Gln | Tyr | Thr | Leu |
| | 560 | | | | 565 | | | | 570 | | | | | |
| Gly | Asn | Ser | Leu | Trp | Phe | Pro | Val | Gly | Gly | Phe | Met | Gln | Gln | Gly | Ser |
| 575 | | | | 580 | | | | 585 | | | | | | 590 |
| Glu | Ile | Met | Pro | Arg | Ala | Leu | Ser | Thr | Arg | Cys | Val | Ser | Gly | Val | Trp |
| | | | 595 | | | | 600 | | | | 605 | | | |
| Trp | Ala | Phe | Thr | Leu | Ile | Ile | Ile | Ser | Ser | Tyr | Thr | Ala | Asn | Leu | Ala |
| | | | 610 | | | | 615 | | | | 620 | | | |
| Ala | Phe | Leu | Thr | Val | Gln | Arg | Met | Glu | Val | Pro | Val | Glu | Ser | Ala | Asp |
| | | 625 | | | | 630 | | | | 635 | | | | |
| Asp | Leu | Ala | Asp | Gln | Thr | Asn | Ile | Glu | Tyr | Gly | Thr | Ile | His | Ala | Gly |
| | 640 | | | | 645 | | | | 650 | | | | | |
| Ser | Thr | Met | Thr | Phe | Phe | Gln | Asn | Ser | Arg | Tyr | Gln | Thr | Tyr | Gln | Arg |
| 655 | | | | 660 | | | | 665 | | | | | | 670 |
| Met | Trp | Asn | Tyr | Met | Gln | Ser | Lys | Gln | Pro | Ser | Val | Phe | Val | Lys | Ser |
| | | | 675 | | | | 680 | | | | 685 | | | |
| Thr | Glu | Glu | Gly | Ile | Ala | Ala | Val | Leu | Asn | Ser | Arg | Tyr | Ala | Phe | Leu |
| | | | 690 | | | | 695 | | | | 700 | | | |
| Leu | Glu | Ser | Thr | Met | Asn | Glu | Tyr | His | Arg | Arg | Leu | Asn | Cys | Asn | Leu |
| | | 705 | | | | 710 | | | | 715 | | | | |
| Thr | Gln | Ile | Gly | Gly | Leu | Leu | Asp | Thr | Lys | Gly | Tyr | Gly | Ile | Gly | Met |
| | 720 | | | | 725 | | | | 730 | | | | | |
| Pro | Leu | Gly | Ser | Pro | Phe | Arg | Asp | Glu | Ile | Thr | Leu | Ala | Ile | Leu | Gln |
| 735 | | | | 740 | | | | 745 | | | | | | 750 |
| Leu | Gln | Glu | Asn | Asn | Arg | Leu | Glu | Ile | Leu | Lys | Arg | Lys | Trp | Trp | Glu |
| | | | | 755 | | | | 760 | | | | | 765 | |
| Gly | Gly | Arg | Cys | Pro | Lys | Glu | Glu | Asp | His | Arg | Ala | Lys | Gly | Leu | Gly |
| | | | 770 | | | | 775 | | | | 780 | | | |
| Met | Glu | Asn | Ile | Gly | Gly | Ile | Phe | Ile | Val | Leu | Ile | Cys | Gly | Leu | Ile |
| | | 785 | | | | 790 | | | | 795 | | | | |
| Ile | Ala | Val | Phe | Val | Ala | Val | Met | Glu | Phe | Ile | Trp | Ser | Thr | Arg | Arg |
| | 800 | | | | 805 | | | | 810 | | | | | |
| Ser | Ala | Glu | Ser | Glu | Glu | Val | Ser | Val | Cys | Gln | Glu | Met | Leu | Gln | Glu |
| 815 | | | | 820 | | | | 825 | | | | | | 830 |
| Leu | Arg | His | Ala | Val | Ser | Cys | Arg | Lys | Thr | Ser | Arg | Ser | Arg | Arg | Arg |
| | | | | 835 | | | | 840 | | | | | | 845 |

| Arg | Arg | Pro | Gly | Gly | Pro | Ser | Arg | Ala | Leu | Leu | Ser | Leu | Arg | Ala | Val |
|-----|-----|-----|-----|-----|-----|-----|-----|-----|-----|-----|-----|-----|-----|-----|-----|
|     |     |     | 850 |     |     |     |     | 855 |     |     |     |     | 860 |     |     |
| Arg | Glu | Met | Arg | Leu | Ser | Asn | Gly | Lys | Leu | Tyr | Ser | Ala | Gly | Ala | Gly |
|     |     | 865 |     |     |     |     | 870 |     |     |     |     | 875 |     |     |     |
| Gly | Asp | Ala | Gly | Ser | Ala | His | Gly | Gly | Pro | Gln | Arg | Leu | Leu | Asp | Asp |
|     | 880 |     |     |     |     | 885 |     |     |     |     | 890 |     |     |     |     |
| Pro | Gly | Pro | Pro | Ser | Gly | Ala | Arg | Pro | Ala | Ala | Pro | Thr | Pro | Cys | Thr |
| 895 |     |     |     |     | 900 |     |     |     |     | 905 |     |     |     |     | 910 |
| His | Val | Arg | Val | Cys | Gln | Glu | Cys | Arg | Arg | Ile | Gln | Ala | Leu | Arg | Ala |
|     |     |     |     | 915 |     |     |     |     | 920 |     |     |     |     | 925 |     |
| Ser | Gly | Ala | Gly | Ala | Pro | Pro | Arg | Gly | Leu | Gly | Val | Pro | Ala | Glu | Ala |
|     |     |     | 930 |     |     |     |     | 935 |     |     |     |     | 940 |     |     |
| Thr | Ser | Pro | Pro | Arg | Pro | Arg | Pro | Gly | Pro | Ala | Gly | Pro | Arg | Glu | Leu |
|     |     | 945 |     |     |     |     | 950 |     |     |     |     | 955 |     |     |     |
| Ala | Glu | His | Glu |
|     |     |     |     |
|     | 960 |     |     |

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:3:

GGGGTTTAAG CTTGGCCCTG TGGACTGCCC TCTCC       35

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:4:

GAAGTCCATG GTGGTGAGGA TG       22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:5:

CATCCTCACC ACCATGGACT TC       22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:6:

```
TCCGGTTGAT GAGCTCGCCA AC                                              22
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:7:

```
GTTGGCGAGC TCATCAACCG GA                                              22
```

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:8:

```
GCCCAGCGGC ATGCCAATGC CG                                              22
```

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:9:

```
CGGCATTGGC ATGCCGCTGG GC                                              22
```

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:10:

```
GGGGTTTAAG CTTATTCCAA CAGGGGCTGC GATGT                                35
```

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear (i i) MOLECULE TYPE: Other nucleic acid;
        (A) DESCRIPTION: Synthetic DNA oligonucleotide (x i) SEQUENCE DESCRIPTION: SEQ ID NO:11:

AGCTTGCGGC CGC                                                                                      13

(2) INFORMATION FOR SEQ ID NO:12:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i v) ANTI-SENSE: YES (x i) SEQUENCE DESCRIPTION: SEQ ID NO:12:

GCGGCCGCA                                                                                            9

(2) INFORMATION FOR SEQ ID NO:13:

(i) SEQUENCE CHARACTERISTICS:
        (A) LENGTH: 16 amino acids
        (B) TYPE: amino acid
        (D) TOPOLOGY: linear (i i) MOLECULE TYPE: peptide (x i) SEQUENCE DESCRIPTION: SEQ ID NO:13:

Met  Val  Gly  Glu  Leu  Ile  Asn  Arg  Gln  Lys  Ala  Asp  Leu  Ala  Val  Ala
 1                   5                        10                       15

(2) INFORMATION FOR SEQ ID NO:14:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:14:

ATGGTTGGCG AGCTCATCAA CCGGCAGAAG GCAGACCTGG CTGTGGC                                                 47

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:15:

ATGGTTGGCG AGCTCATCAA CCGG                                                                          24

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: double
        (D) TOPOLOGY: linear ( i i ) MOLECULE TYPE: DNA (genomic)

( x i ) SEQUENCE DESCRIPTION: SEQ ID NO:16:

AAGGCAGACC TGGCTGTGGC C    21

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Met Val Gly Glu Leu Ile Asn Arg
1               5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Lys Ala Asp Leu Ala Val Ala
1               5

( 2 ) INFORMATION FOR SEQ ID NO:19:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

CTGCCAGGTG CTCTCATCAC TGCGCATGGC TGCAATCCTG GATGATCAGA CAGTGTGTGG    60

CCGCGGTGAG CGTCTGGCCT TGGCCTTGGC CCGGGAGCAG    100

( 2 ) INFORMATION FOR SEQ ID NO:20:

( i ) SEQUENCE CHARACTERISTICS:
        ( A ) LENGTH: 79 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

GGATGAGGCA CAAGAATCAC TTGGACCGGG AGGCAGGAGT TGCAGTGAGC GTCTGGCCTT    60

GGCCTTGGCC CGGGAGCAG    79

( 2 ) INFORMATION FOR SEQ ID NO:21:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: peptide (x i) SEQUENCE DESCRIPTION: SEQ ID NO:21:

```
Met Pro Ala Glu Leu Leu Leu Leu Leu Ile Val Ala Phe Ala Ser Pro
 1               5                      10                  15
Ser Cys Gln Val Leu Ser Ser Leu Arg Met Ala Ala Ile Leu Asp Asp
            20                  25                  30
Gln Thr Val Cys Gly Arg Gly Glu Arg Leu Ala Leu Ala Leu Ala Arg
            35              40                  45
Glu Gln Ile Asn Gly Ile Ile Glu Val Pro Ala Lys Ala Arg Val Glu
        50              55                  60
Val Asp Ile Phe Glu Leu Gln Arg Asp Ser Gln Tyr Glu Thr Thr Asp
 65                 70                  75                      80
Thr Met Cys Gln Ile Leu Pro Lys
                85
```

(2) INFORMATION FOR SEQ ID NO:22:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (x i) SEQUENCE DESCRIPTION: SEQ ID NO:22:

```
Asp Glu Ala Gln Glu Ser Leu Gly Pro Gly Gly Arg Ser Cys Ser Glu
 1               5                      10                  15
Arg Leu Ala Leu Ala Leu Ala Arg Glu Gln Ile Asn Gly Ile Ile Glu
            20                  25                  30
Val Pro Ala Lys Ala Arg Val Glu Val Asp Ile Phe Glu Leu Gln Arg
            35              40                  45
Asp Ser Gln Tyr Glu Thr Thr Asp Thr Met Cys Gln Ile Leu Pro Lys
        50              55                  60
```

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (x i) SEQUENCE DESCRIPTION: SEQ ID NO:23:

GGGGTTTAAG CTTGAGCGTC GTCCTCTTCC TGGT      34

(2) INFORMATION FOR SEQ ID NO:24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (x i) SEQUENCE DESCRIPTION: SEQ ID NO:24:

GGGGTTTAAG CTTGTGAAGA ACCACCAGAC GCCG      34